United States Patent
Pless et al.

(10) Patent No.: US 9,114,260 B2
(45) Date of Patent: Aug. 25, 2015

(54) IMPLANTABLE SYSTEM ENABLING RESPONSIVE THERAPY FOR PAIN

(71) Applicant: NeuroPace, Inc., Mountain View, CA (US)

(72) Inventors: Benjamin D Pless, Atherton, CA (US); Michael Sasha John, Larchmont, NY (US)

(73) Assignee: NeuroPace, Inc., Mountain View, CA (US)

( * ) Notice: Subject to any disclaimer, the term of this patent is extended or adjusted under 35 U.S.C. 154(b) by 0 days.

(21) Appl. No.: 14/321,287

(22) Filed: Jul. 1, 2014

(65) Prior Publication Data

US 2014/0323958 A1   Oct. 30, 2014

Related U.S. Application Data

(60) Continuation of application No. 14/043,599, filed on Oct. 1, 2013, now Pat. No. 8,805,520, which is a continuation of application No. 13/011,917, filed on Jan. 23, 2011, now Pat. No. 8,583,239, which is a division of application No. 11/374,380, filed on Mar. 13, 2006, now Pat. No. 7,894,805.

(51) Int. Cl.
| | | |
|---|---|---|
| *A61N 1/00* | (2006.01) | |
| *A61N 1/36* | (2006.01) | |
| *A61M 5/172* | (2006.01) | |
| *A61N 2/00* | (2006.01) | |
| *A61N 5/06* | (2006.01) | |

(52) U.S. Cl.
CPC ......... *A61N 1/36071* (2013.01); *A61M 5/1723* (2013.01); *A61N 2/006* (2013.01); *A61N 5/0622* (2013.01); *A61M 2005/1726* (2013.01)

(58) Field of Classification Search
CPC ............ A61M 2005/1726; A61M 5/1723; A61N 1/36071; A61N 2/006; A61N 5/0622
USPC ................................................. 607/46
See application file for complete search history.

(56) References Cited

U.S. PATENT DOCUMENTS

| | | |
|---|---|---|
| 5,938,689 A | 8/1999 | Fischell et al. |
| 6,006,124 A | 12/1999 | Fischell et al. |
| 6,016,449 A | 1/2000 | Fischell et al. |
| 6,061,593 A | 5/2000 | Fischell et al. |
| 6,128,538 A | 10/2000 | Fischell et al. |
| 6,134,474 A | 10/2000 | Fischell et al. |
| 6,161,045 A | 12/2000 | Fischell et al. |
| 6,230,049 B1 | 5/2001 | Fischell et al. |
| 6,353,754 B1 | 3/2002 | Fischell et al. |

(Continued)

OTHER PUBLICATIONS

Apkarian A V, Bushnell M C, Treede R D, Zubieta J K. Human brain mechanisms of pain perception and regulation in health and disease. Eur J Pain. Aug. 2005;9(4):463-84.

(Continued)

*Primary Examiner* — George Manuel
(74) *Attorney, Agent, or Firm* — Arent Fox LLP

(57) ABSTRACT

An implantable neurostimulator system for treating pain includes scheduled and responsive therapy capabilities including responsive stimulation applied to the brain and peripheral sections of the nervous system. Methods for treating chronic nociceptive, neuropathic, and psychogenic pain employ an inventive system to advantageously reduce multiple symptoms and components of pain and to address underlying causes of pain.

15 Claims, 17 Drawing Sheets

(56) References Cited

U.S. PATENT DOCUMENTS

| | | | |
|---|---|---|---|
| 6,354,299 B1 | 3/2002 | Fischell et al. | |
| 6,360,122 B1 | 3/2002 | Fischell et al. | |
| 6,402,678 B1 | 6/2002 | Fischell et al. | |
| 6,427,086 B1 | 7/2002 | Fischell et al. | |
| 6,459,936 B2 | 10/2002 | Fischell et al. | |
| 6,466,822 B1 | 10/2002 | Pless | |
| 6,473,639 B1 | 10/2002 | Fischell et al. | |
| 6,480,743 B1 | 11/2002 | Kirkpatrick et al. | |
| 6,529,774 B1 | 3/2003 | Greene | |
| 6,591,137 B1 | 7/2003 | Fischell et al. | |
| 6,591,138 B1 | 7/2003 | Fischell et al. | |
| 6,597,954 B1 | 7/2003 | Fischell et al. | |
| 6,622,048 B1 | 9/2003 | Mann et al. | |
| 6,647,296 B2 | 11/2003 | Fischell et al. | |
| 6,654,642 B2 * | 11/2003 | North et al. | 607/59 |
| 6,662,035 B2 | 12/2003 | Sochor | |
| 6,690,974 B2 | 2/2004 | Archer et al. | |
| 6,721,603 B2 | 4/2004 | Zabara et al. | |
| 6,735,475 B1 | 5/2004 | Whitehurst et al. | |
| 6,810,285 B2 | 10/2004 | Pless et al. | |
| 6,944,501 B1 | 9/2005 | Pless | |
| 7,089,059 B1 | 8/2006 | Pless | |
| 7,110,820 B2 | 9/2006 | Tcheng | |
| 7,136,695 B2 | 11/2006 | Pless et al. | |
| 7,174,213 B2 | 2/2007 | Pless | |
| 7,177,674 B2 | 2/2007 | Echauz et al. | |
| 7,184,837 B2 | 2/2007 | Goetz | |
| 7,198,603 B2 * | 4/2007 | Penner et al. | 600/486 |
| 7,277,748 B2 | 10/2007 | Wingeier et al. | |
| 7,294,101 B2 | 11/2007 | Fischell et al. | |
| 7,321,792 B1 | 1/2008 | Min et al. | |
| 7,353,065 B2 | 4/2008 | Morrell | |
| 7,494,458 B2 | 2/2009 | Fischell et al. | |
| 7,601,116 B2 | 10/2009 | Fischell et al. | |
| 2003/0144711 A1 | 7/2003 | Fischell et al. | |
| 2003/0195590 A1 | 10/2003 | Carter | |
| 2003/0233053 A1 | 12/2003 | Woolf et al. | |
| 2005/0049654 A1 | 3/2005 | Lathrop | |
| 2006/0129204 A1 | 6/2006 | Pless et al. | |
| 2007/0179557 A1 | 8/2007 | Maschino et al. | |
| 2007/0213784 A1 | 9/2007 | Pless | |
| 2010/0137937 A1 | 6/2010 | Pless et al. | |

OTHER PUBLICATIONS

Drewes A M, Sami S A, Dimcevski G, Nielsen K D, Funch-Jensen P, Valeriani M, Arendt-Nielsen L. "Cerebral processing of painful oesophageal stimulation. A study based on independent component analysis of the EEG". Gut. 2005.

Krause P, Forderreuther S, Straube A. "TMS motor cortical brain mapping in patients with complex regional pain syndrome type I". Clin. Neurophysiol. Jan. 2006;117(1):169-76. Epub Dec. 2, 2005.

Kumar et al., "Deep Brain Stimulation for Intractable Pain: A 15-Year Experience," Neurosurgery 40(4): 736-747, Apr. 1997.

D. Nandi et al.. "Thalamic field potentials in chronic central pain treated by periventricular gray stimulation—a series of eight cases," Pain 101 (2003) 97-107.

Sarnthein J, Stern J, Aufenberg C, Rousson V, Jeanmonod D. "Increased EEG power and slowed dominant frequency in patients with neurogenic pain". Brain. Jan. 2006;129 (pt 1):55-64.

Weiland and Anderson, "Chronic Neural Stimulation with Thin-Film, Iridium Oxide Electrodes," IEEE Transactions on Biomedical Engineering, 47: 911-918 (2000).

* cited by examiner

IMPLANTABLE SYSTEM ENABLING RESPONSIVE THERAPY FOR PAIN

RELATED APPLICATIONS

This application is a continuation of U.S. patent application Ser. No. 14/043,599, now U.S. Pat. No. 8,805,520, filed Oct. 1, 2013, which is a continuation application of U.S. patent application Ser. No. 13/011,917, now U.S. Pat. No. 8,583,239, filed Jan. 23, 2011, which is a divisional application of U.S. patent application Ser. No. 11/374,380, now U.S. Pat. No. 7,894,905, filed Mar. 13, 2006, each of which are incorporated by reference herein in their entirety.

FIELD OF THE INVENTION

The invention relates to systems and methods for treating brain disorders, and more particularly to treating pain and related conditions with automatically delivered therapies.

BACKGROUND OF THE INVENTION

Chronic pain, commonly defined as pain that lasts at least six months, is a major medical problem worldwide. Currently used treatment options often fail to relieve all of a patient's symptoms and are associated with significant side effects. Some estimates place the burden as high as US$100 billion per year in the United States alone for the effects of chronic pain including lost productivity and medical expenses.

Pain in general is categorized into three types. Nociceptive pain is the central nervous system's reaction to tissue injury. Nociceptive pain is usually time-limited and tends to decrease as the injury heals. In some cases, such as arthritis and cancer pain, it does not necessarily decrease over time. Regardless of cause, nociceptive pain can be long-term and debilitating.

Neuropathic pain arises out of damage to the central nervous system itself, causing signals to be erroneously interpreted as physical pain. This category of pain includes phantom limb pain in amputees and other types of central pain, including allodynia and hyperalgesia. Some studies consider tinnitus, a chronic "ringing of the ears," to be a form of neuropathic pain caused by nerve damage in the auditory system.

Some patients experience combinations of nociceptive and neuropathic pain; in many cases they are mutually reinforcing.

Psychogenic pain is either entirely psychological or without other adequate known medical cause and is generally rare. But to the patient experiencing psychogenic pain, it is potentially very disabling.

The therapy of first resort for nociceptive pain is typically nonsteroidal anti-inflammatory drugs (commonly known as NSAIDs). This category of drugs includes ibuprofen (ADVIL®, MOTRIN®), naproxen (ALEVE®), and celecoxib (CELEBREX®.). They work by blocking cyclooxygenase enzymes, both COX-1 and COX-2 in the case of traditional NSAIDs (such as ibuprofen and naproxen), and primarily COX-2 in the case of the more recent drugs (such as celecoxib). The inhibition of COX-1 may lead to gastrointestinal side effects, and recently, COX-2 specific inhibitors have been linked to an increased risk of myocardial infarction and stroke. There may also be adverse renal effects in all cases.

In more serious cases of chronic pain, opioids are frequently prescribed. This category of drugs includes morphine, codeine, fentanyl, and oxycodone. While treatment with opioids is frequently successful, serious side effects include sedation, respiratory depression, constipation, development of tolerance, and in many cases, addiction and abuse.

For neuropathic pain, antidepressants and anticonvulsives have been found to be useful. Tricyclic antidepressants such as amitriptylene, imipramine, doxepine, clomipramine and trimipramine are useful in some cases, but have significant side effects including sedation, arrhythmia, and constipation. SSRI antidepressants (fluoxetine, paroxetine, etc.) have not been found to be as effective in most cases. Anticonvulsives such as carbamazepine, gabapentin, and phenytoin also provide relief in some patients, but the side effects of these drugs include sedation, liver and kidney dysfunction, and aplastic anemia.

Antidepressants are also used in the treatment of neuropathic pain with some success. As set forth above, side effects do occur.

All of the above drug therapies are useful in treating various cases of chronic pain, but the side effect profiles and ineffectiveness for some patients may cause drug therapy to be contraindicated in a relatively significant portion of the population needing relief.

Externally applied non-drug therapies such as transcutaneous electrical nerve stimulation (TENS) and acupuncture are inconvenient, as they typically require the participation of a clinician, and may not provide long-term relief for many patients.

Implantable spinal cord and peripheral nerve stimulators are commercially available. Some work has been done with deep brain stimulators, but such devices are generally configured to provide a constant (or repeating intermittent) signal to a portion of the brain, which may lead to deficit in the area being stimulated or adjacent areas, and may also result in side effects. The application of continuous or semi-continuous stimulation does not require a particularly complex device, but more power is required than would be necessary in a device that stimulated only selectively. And there is some risk of habituation with chronic stimulation.

Spinal cord stimulation and to some extent TENS and implantable peripheral nerve stimulation are thought to provide relief consistent with the "gate control" theory of pain, in which signals in large and small nerve fibers interact to provide pain perception. Simplified to some extent, signals in large nerve fibers primarily represent non-painful stimuli such as touch, and tend to activate neurons inhibiting pain. When pain is present, signals in small nerve fibers inhibit the inhibitory neurons, thereby facilitating pain perception. Spinal cord stimulation (SCS), TENS, and peripheral nerve stimulation (PNS) all tend to control the spike rate of neurons in large fibers (which are more easily activated than small fibers), thereby favoring touch over pain. There is also differential activation of afferent nerves (ascending signals) over efferent (descending). SCS in particular is thought to act through inhibition, possibly through descending inhibitory pathways.

Implantable drug pumps are a promising therapy for chronic pain, allowing analgesic therapeutic agents to be targeted directly on the tissue from which the pain arises. However, in many cases, implantable drug pumps that deliver drugs outside of brain targets are ineffective. In addition to having side effects and controlled substance issues, drug pumps require maintenance and may tend to adversely affect the function of surrounding tissue.

Studies of the brain using functional imaging techniques have identified a number of brain regions that are involved in pain processing. These include but are not limited to the anterior cingulate cortex, prefrontal cortex, insular cortex, thalamus and portions of the somatosensory cortex, for example those corresponding to regions of pain (see, e.g., Krause P, Forderreuther S, Straube A. TMS motor cortical brain mapping in patients with complex regional pain syndrome type I. *Clin. Neurophysiol.* 2006 January; 117(1):169-76. Epub 2005 Dec. 2; and Apkarian A V, Bushnell M C, Treede R D, Zubieta J K. Human brain mechanisms of pain perception and regulation in health and disease. *Eur J Pain.* 2005 August; 9(4):463-84, both incorporated by reference herein). Accordingly, surgical and ablative techniques, performed peripherally and in the central nervous system, are gaining favor in particularly difficult-to-control cases of chronic pain. Non-surgical resection and ablation can be performed using radiological Gamma Knife and linear accelerator apparatus. Great precision is required, as surgery and ablation are typically irreversible, and any deficits sustained by the patient are in many cases permanent. And even with such great risks, the success of such procedures is uncertain.

Most of the approaches to treating pain set forth above have side effects, and even when the treatment is effective, the side effects can still be disabling to the patient. Moreover, current treatment options are frequently subtherapeutic and fail to resolve the multiple components of pain perception. Accordingly, there is a need for a responsive implantable system capable of deterring, ameliorating the symptoms of, and in some cases the underlying causes of, various chronic pain conditions.

SUMMARY OF THE INVENTION

As facilitated by the current invention, appropriate modulation of the function of various brain and nervous system structures can alleviate symptoms associated with chronic pain, including nociceptive, neuropathic, and psychogenic pain. In some cases, a coordinated strategy treating multiple structures and areas may be useful to treat various components of the pain experienced by a patient.

Pain is generally regarded as having a sensory component (the local discomfort caused by the pain itself) and an affective component (the overall "soreness" and discomfort associated with experiencing pain, and its motivational correlates including fear and general distress). Some researchers also recognize a cognitive component, in which a patient's perception of pain leads to secondary psychological effects. Known psychological disorders are often observed in patients with chronic pain.

In systems and methods according to the present invention, therapy for chronic pain set forth above is provided by means of a device that is able to provide responsive and programmed electrical stimulation to relevant portions of the brain and peripheral nervous system. Such therapy is considered effective for nociceptive, neuropathic, and psychogenic pain, and may treat sensory, affective, and cognitive components.

In an embodiment of the invention, a device is implanted in the cranium and attached to leads with electrodes at the distal end of each lead. The electrodes are placed in or adjacent to one or more structures of interest whether in the form of a nerve electrode, a brain depth electrode, a plate electrode, an array of electrodes, or a brain subdural electrode. A single electrode or multiple electrodes may be implanted.

An embodiment of the system includes multiple devices or modules, each operating essentially autonomously but in a correlated fashion to treat the various components of a patient's pain in different parts of the patient's body or brain. In a separate embodiment, the operations of the multiple devices are coordinated by a "master device" which communicates with, and modifies the operation of the other devices. The master device can be a patient controller, located external to the patient.

The system has a sensing function that responds to changes in, or a detection of, a biological marker. Such biological markers could be changes in electrical activity, optically sensed data, changes in cerebral blood flow, metabolism, and constituents, changes in concentration of inhibitory or excitatory neurochemicals, changes in proteins or other gene products, or changes in temperature or markers of metabolic rate. Sensing electrodes or other sensors, including but not limited to thermal sensors, optical sensors, and chemical detectors, are placed over a cortical structure, within the brain, in a spinal location, within another desired part of the patient's body or even at some distance from an area that is to be sensed.

Responsive therapy is provided to at least one location within the central nervous system. Such therapy may include electrical stimulation, optical stimulation, drug delivery or changes in temperature. In addition, therapy delivery can be programmed by the physician or patient in response to the patient's symptoms.

It is anticipated that the part of the brain where the system senses neural activity may be different than the location where therapy is delivered. For example therapy may be delivered to the motor cortex or to the periventricular gray area, while the system senses in the sensory region of the thalamus. In this case the system is adapted to detect low frequency oscillatory signals in the thalamus, and to automatically adjust stimulation to minimize the signal representative of pain. The device also includes the capability for therapy to be triggered by the patient.

The system monitors signals representative of pain, and maintains diagnostics of the extent of pain over time in the patient, and the response of the signals representative of pain to therapy. The diagnostics are made available to the clinician to aid in the care of the patient. Having a means to monitor pain without requiring the patient to report levels of pain (which is very subjective and subject to abuse particularly for patients on medications) is a major improvement in caring for these patients. In the case where the device also includes the capability for therapy to be triggered by the patient, the diagnostics may also keep track of the patient's requests for therapy.

Such a system could provide benefit for those individuals with pain that is refractory to traditional treatments and for those who experience drug related side effects that limit quality of life. In addition, a device therapy as described above can be anticipated to have a more favorable safety profile than cortical resection or cortical lesion, and will be modifiable across individuals and over time and is reversible if the desired effects are not achieved. The precise portions of the patient's brain and body over which therapy is optimally applied may differ from individual to individual and by the symptoms experienced. The electrodes over which therapy is applied can be adjusted according to the patient's short and long-term response.

An embodiment of the invention allows for the sensing and identifying signals representing pain in one or more of the patient's primary somatosensory cortex (SI), secondary somatosensory cortex (SII), anterior cingulate cortex, prefrontal cortex, insular cortex, thalamus, the sensory area of the thalamus, spinal cord, and peripheral nerves. The invention further allows for treatment in one or more of the thalamus, motor cortex, brain stem, periaqueductal gray, periventricular gray, precentral gyms, cingulate, caudate, amygdala, parietal cortex, spinal cord, and peripheral nerves.

An embodiment of the device provides continuous monitoring of electrocorticographic signals. This capability can identify disturbances in brain electrical activity over various portions of the brain that cannot be adequately monitored by scalp EEG due to their distance from the recording electrodes and the significant filtering effect of skull and scalp. This is an especially important capability of the system because pain is likely to be accompanied by dynamic electrographic disturbances. This device will also enable continuous monitoring of other biological markers that may reveal signals of disease and disease symptoms. Identifying these biological markers via continued observation with a system according to the invention will contribute to knowledge regarding the underlying pathophysiology of these diseases and will provide information that may open new avenues for targeted therapy.

Direct stimulation of the nervous system using a device according to the invention provides advantages over drugs, resective and lesion-based surgery, and over continuous deep-brain stimulation. Targeted and selective therapy promises longer battery life. Additionally, responsive stimulation can self modulate to more adjust to the patient's changing condition, and to deliver more optimal therapy over time. Delivery of therapy has an effect that extends beyond the immediate duration of the therapy. As described above, an exemplary device utilizes two leads of four electrodes each. Using either depth or subdural leads (or a combination of the two), electrodes can be applied over much of one or two structures of interest, and multiple modules in a system according to the invention can target even more structures. Within the framework of the implanted configuration, preferred stimulation electrodes can be configured over time as a patient's symptoms are observed. Stimulation may be quite focal, using adjacent electrodes as anode and cathode, or can be applied to relative large volumes of tissue by utilizing all eight electrodes referred to the can of the device.

Another advantage of the implantable neurostimulator system is the capacity to apply modifiable stimulation settings. In an embodiment of the invention, pulse widths can be set between 40 and 1000 microseconds, pulse frequency may range between 1 and 333 Hz, and current can be adjusted between 0.5 and 12 milliamps. These settings may be set by the clinician or automatically adjusted in a responsive system. This ensures that patients receive effective pulse settings over changing medical conditions while minimizing adverse effects. Non-pulsatile electrical stimulation may also be advantageously employed. It is reasonable to assume that individual patients will differ in terms of the optimal stimulus settings. Drug delivery, thermal stimulation, magnetic stimulation, and optical stimulation are alternative therapy modalities.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 2:
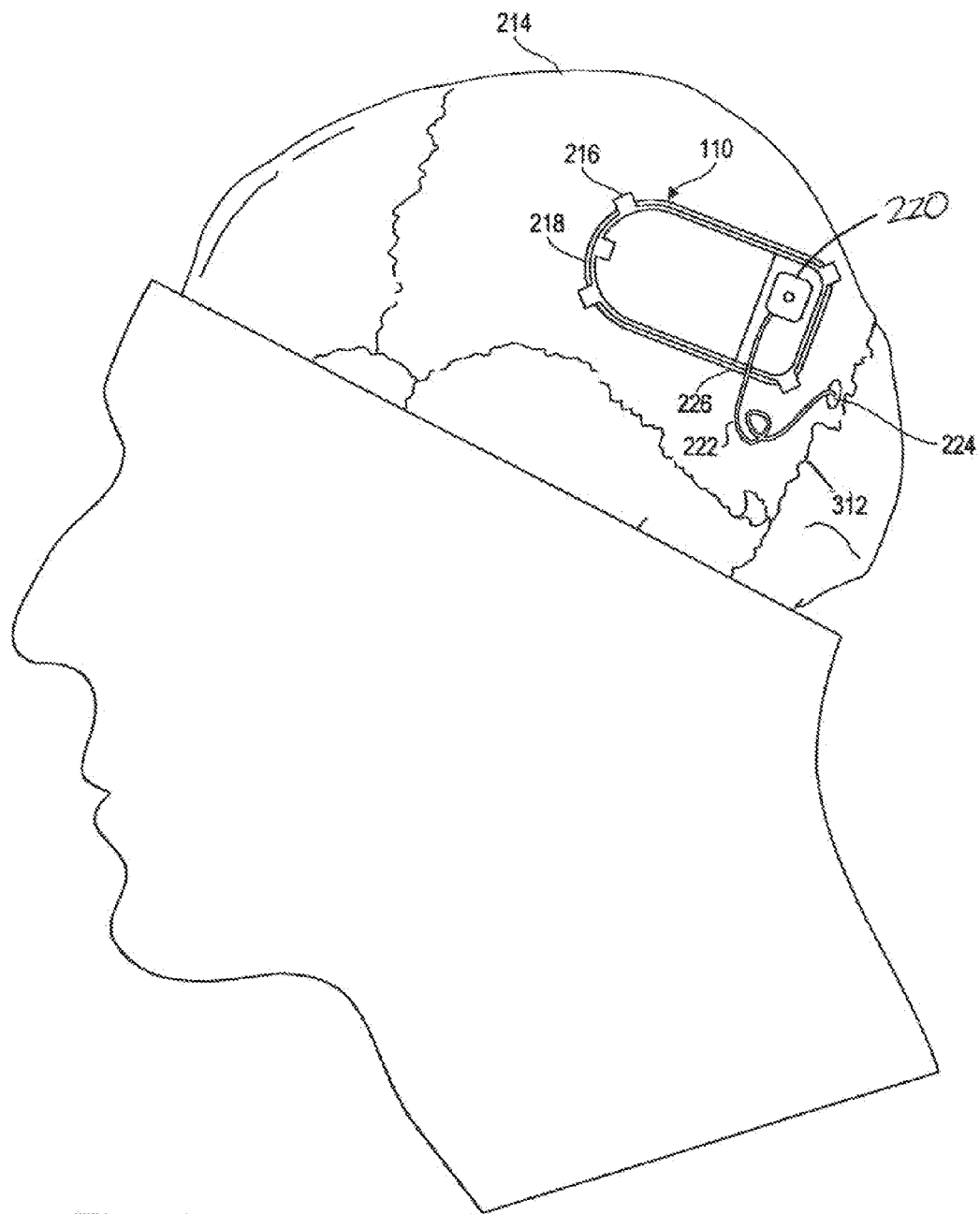
FIG. 2 is a schematic illustration of a patient's cranium showing the implantable neurostimulator of FIG. 1 as implanted, including a lead extending to the patient's brain.

FIG. 2 depicts an intracranial implantation of an implantable neurostimulator device 110 according to the invention, which in one embodiment is a small self-contained responsive neurostimulator. As the term is used herein, a responsive neurostimulator is a device capable of detecting or predicting neurological events and conditions, such as abnormal electrical activity, and providing electrical stimulation to neural tissue in response to that activity, where the electrical stimulation is specifically intended to terminate the abnormal activity, treat a neurological event, prevent an unwanted neurological event from occurring, or lessen the severity or frequency of certain symptoms of a neurological disorder. Event detection can include, for example, measurement of related signatures, such as one or more pain signatures, each of which can be a component of the event that is at least partially related to a symptom of the disorder. As disclosed herein, the responsive neurostimulator detects abnormal neurological activity in the central nervous system or peripheral nervous system (e.g., spine, vagus nerve, peripheral pain fibers) by systems and methods according to the invention.

Preferably, an implantable device according to the invention is capable of detecting or predicting any kind of neurological event that has a representative electrographic signature, such as a pain signature. While the disclosed embodiment is described primarily as responsive to symptoms and conditions present in chronic pain, it should be recognized that it is also possible for a multifunction device to respond to other types of neurological disorders, such as epilepsy, movement disorders (e.g. the tremors characterizing Parkinson's disease), migraine headaches, and psychiatric disorders. Preferably, neurological events representing any or all of these afflictions can be detected when they are actually occurring, in an onset stage, or as a predictive precursor before clinical symptoms begin.

In the disclosed embodiment, the neurostimulator device 110 is implanted intracranially in a patient's parietal bone 210, in a location anterior to the lambdoid suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 (FIG. 1) but partially or fully external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating pain, chronic pain and related symptoms, including psychological, emotional, sensory, and cognitive effects, by detecting neurophysiological signatures of related conditions, symptoms, or their onsets or precursors, and preventing and/or relieving such conditions and symptoms.

In an alternative embodiment of the invention, the device 110 is not a responsive neurostimulator, but is an apparatus capable of detecting signatures of neurological conditions and events and performing actions (other than electrical stimulation) in response thereto. For example, the actions performed by such an embodiment of the device 110 need not be therapeutic, but may only involve data recording or transmission, providing warnings to the patient, providing a patient with messages (e.g., "take medication" or "your depression score is increasing"), alerting a physician, or any of a number of known alternative actions. Additionally, using an external patient programmer, the patient can induce data collection when subjective experiences occur and can enter event tags (e.g., "pain has decreased" or "feel depressed"). Such a device will typically act as a diagnostic device when interfaced with external equipment. A device according to the invention, whether it delivers therapy or acts solely as a diagnostic device, is advantageously capable of storing diagnostic information for later retrieval by a programmer.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone 310 anterior to the lambdoid suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode or other sensor (e.g., one of the sensors 412-418 of FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al. for "Means and Methods for the Placement of Brain Electrodes" issued Dec. 21, 1999, which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be in the interior of the device 110 or provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of breaking the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

As will be discussed in further detail below, the leads attached to the device 110 are implanted in one or more structures of interest, in the brain (including cortical structures and deep brain structures), other portions of the central nervous system, and the peripheral nervous system. It will be noted that lead placement is patient specific; different symptoms and conditions call for different structures to be targeted—for example, patients with central pain may benefit primarily from central stimulation, and patients with peripheral pain (i.e., nociceptive pain arising from peripheral locations) may benefit from peripheral nerve stimulation. Patients with idiopathic pain (i.e., pain with no known cause) may benefit from some combination of central and peripheral stimulation depending on the patient's individual clinical circumstances. This will be discussed in further detail below.

Figure 3:
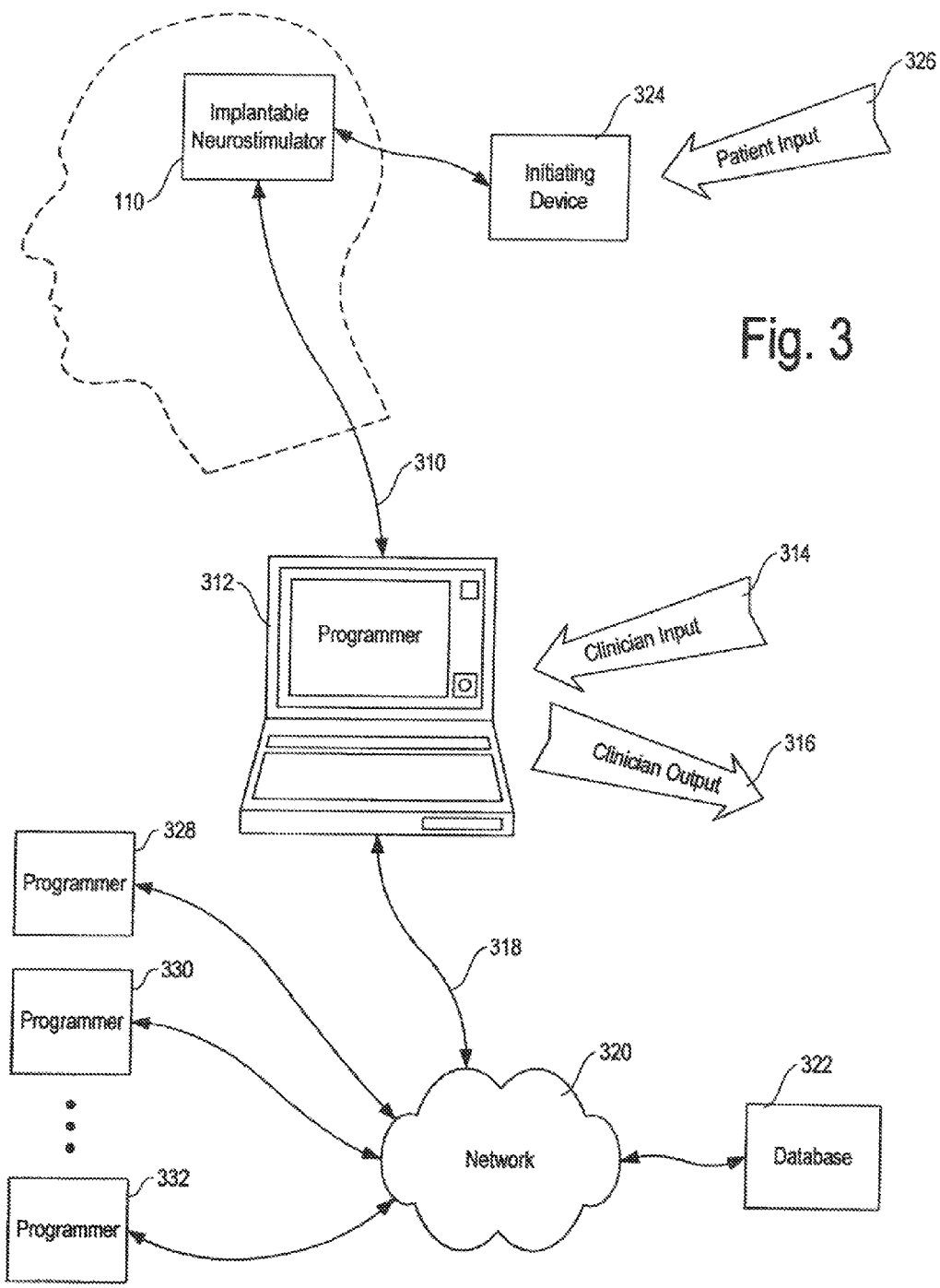
FIG. 3 is a block diagram illustrating a system context in which an implantable neurostimulator according to the invention is implanted and operated.

As stated above, and as illustrated in FIG. 3, a neurostimulator according to the invention operates in conjunction with external equipment. The implantable neurostimulator device 110 is mostly autonomous (particularly when performing its usual sensing, detection, and stimulation capabilities), but preferably includes a selectable part-time wireless link 310 to external equipment such as a programmer 312. In the disclosed embodiment of the invention, the wireless link 310 is established by moving a wand (or other apparatus) having communication capabilities and coupled to the programmer 312 into communication range of the implantable neurostimulator device 110. The programmer 312 can then be used to manually control the operation of the device, as well as to transmit information to or receive information from the implantable neurostimulator 110. Several specific capabilities and operations performed by the programmer 312 in conjunction with the device will be described in further detail below.

The programmer 312 is capable of performing a number of advantageous operations in connection with the invention. In particular, the programmer 312 is able to specify and set variable parameters in the implantable neurostimulator device 110 to adapt the function of the device to meet the patient's needs, upload or receive data sent from the implantable neurostimulator 110 to the programmer 312 including, but not limited to, stored sensed data such as raw signal waveforms (e.g., collected before and after stimulation, continuously, or periodically), summaries of the sensed information (e.g., statistical summaries such as mean and standard deviation of the count, kind, size, or other aspect of detected events; a count of detected events) parameters, stored diagnostic information relating to observed activity, or logs of actions taken. The programmer 312 can also download or transmit program code and other information to the implantable neurostimulator 110, or command the implantable neurostimulator 110 to perform specific actions or change stimulation, treatment, or recording modes as desired by a physician operating the programmer 312. To facilitate these functions, the programmer 312 is adapted to receive clinician input 314 and provide clinician output 316; data is transmitted between the programmer 312 and the implantable neurostimulator 110 over the wireless link 310. The programmer 312 may be used at a location remote from the implantable neurostimulator 110 if the wireless link 310 is enabled to transmit data over long distances. For example, the wireless link 310 may be established by a short-distance first link between the implantable neurostimulator 110 and a transceiver, with the transceiver enabled to relay communications over long distances to a remote programmer 312, either wirelessly (for example, over a wireless computer network) or via a wired communications link (such as a telephonic circuit or a computer network).

The programmer 312 may also be coupled via a communication link 318 to a network 320 such as the Internet. This allows any information uploaded from the implantable neurostimulator 110, as well as any program code or other information to be downloaded to the implantable neurostimulator 110, to be stored in a database 322 at one or more data repository locations (which may include various servers and network-connected programmers like the programmer 312). This would allow a patient (and the patient's physician) to have access to important data, including past treatment information and software updates, essentially anywhere in the world where there is a programmer (like the programmer 312) and a network connection. Alternatively, the programmer 312 may be connected to the database 322 over a trans-telephonic link such as modem connection.

In yet another alternative embodiment of the invention, the wireless link 310 from the implantable neurostimulator 110 may enable a transfer of data from the neurostimulator 110 to the database 322 without any involvement by the programmer 312. In this embodiment, as with others, the wireless link 310 may be established by a short-distance first link between the implantable neurostimulator 110 and a transceiver (such as a Bluetooth® enabled modem with a wireless port for accepting data or a device operating in the MICS band), with the transceiver enabled to relay communications over long distances to the database 322, either wirelessly (for example, over a wireless computer network) or via a wired communications link (such as trans-telephonically over a telephonic circuit, or over a computer network).

In the disclosed embodiment, the implantable neurostimulator 110 is also adapted to receive communications from an initiating device 324, typically controlled by the patient or a caregiver. Accordingly, patient input 326 from the initiating device 324 is transmitted over a wireless link to the implantable neurostimulator 110; such patient input 326 may be used to cause the implantable neurostimulator 110 to switch modes (on to off and vice versa, for example) or perform an action (e.g., store a record of signal waveform data along with a timestamp and comment from the user). Preferably, the initiating device 324 is able to communicate with the implantable neurostimulator 110 through a communication subsystem 430 (FIG. 4), and possibly via the same kind of link as the programmer 312. The link may be unidirectional (as with the magnet and GMR sensor described below), allowing commands to be passed in a single direction from the initiating device 324 to the implantable neurostimulator 110, but in an alternative embodiment of the invention is bi-directional, allowing status and data to be passed back to the initiating device 324. Accordingly, the initiating device 324 may be a programmable PDA or other hand-held computing device, such as a Palm® device or PocketPC®. Additionally, the initiating device may be compatible with Flash or USB ports and can include wireless communication capabilities so that any computer, PDA, or similar apparatus can be used by the patient to communicate with the neurostimulator device 110. However, a simple form of initiating device 324 may take the form of a permanent magnet, if the communication subsystem 430 (FIG. 4) is adapted to identify magnetic fields and interruptions therein as communication signals.

The implantable neurostimulator 110 (FIG. 1) generally interacts with the programmer 312 (FIG. 3) as described below. Data stored in a memory subsystem 426 (FIG. 4) of the device 110 can be retrieved by the patient's physician through the wireless communication link 310, which operates through the communication subsystem 430 of the implantable neurostimulator 110. In connection with the invention, a software operating program run by the programmer 312 allows the physician to read out a history of neurological events detected including signal information before, during, and after each neurological event, as well as specific information relating to the detection of each neurological event (such as, in one embodiment, the time-evolving energy spectrum of the patient's observed signal across at least a portion of a "spectrogram"). The programmer 312 also allows the physician to specify or alter any programmable parameters of the implantable neurostimulator 110. The software operating program also includes tools for the analysis and processing of recorded signals to assist the physician in developing optimized detection parameters for detecting pain, depression or seizure signatures in each specific patient.

In an embodiment of the invention, the programmer 312 is primarily a commercially available PC, laptop computer, or workstation having a CPU, memory, keyboard, mouse and display, and running a standard operating system such as Microsoft Windows®, Linux®, Unix®, or Apple Mac OS®. It is also envisioned that a dedicated programmer apparatus with a custom software package (which may not use a standard operating system) could be developed. Alternatively, in an alternative embodiment the programmer 312 is a computer or PDA capable of communicating with a program residing on a remote server that sends and receives data from the programmer 312. In this instance the programmer 312 is realized partially as a web-based virtual instrument using a local computer for interacting with the physician/patient and the implanted neurostimulator 110.

When running the computer workstation software operating program, the programmer 312 can process, score, measure, classify, detect events within, and states based upon, sensed signals, and can store, play back and display the patient's electrographic or other sensor signals, as previously stored by the implantable neurostimulator 110 of the implantable neurostimulator device.

The computer workstation software program also has the capability to simulate the detection and prediction of abnormal electrical activity and other symptoms and results of chronic pain. Furthermore, the software program of the present invention has the capability to allow a clinician to create or modify a patient-specific collection of information comprising, in one embodiment, algorithms and algorithm parameters for detection of specific types of activity. The results of tailoring patient-specific detection algorithms and parameters used for neurological activity detection according to the invention will be referred to herein as a detection template or patient-specific template. The patient-specific template, in conjunction with other information and parameters generally transferred from the programmer to the implanted device (such as stimulation parameters, treatment schedules, and other patient-specific information), make up a set of operational parameters for the neurostimulator.

Following the development of a patient-specific template on the programmer 312, the patient-specific template would be downloaded through the communications link 310 from the programmer 312 to the implantable neurostimulator 110.

The patient-specific template is used by a detection subsystem 422 and CPU 428 (FIG. 4) of the implantable neurostimulator 110 to detect conditions indicating treatment should be administered, and can be programmed by a clinician to result in responsive stimulation of the patient's brain, as well as the storage of sensed signals before and after the detection, facilitating later clinician review.

Preferably, the database 322 is adapted to communicate over the network 320 with multiple programmers, including the programmer 312 and additional programmers 328, 330, and 332. It is contemplated that programmers will be located at various medical facilities and physicians' offices at widely distributed locations. Accordingly, if more than one programmer has been used to upload stored signals from a patient's implantable neurostimulator 110, the stored signals will be aggregated via the database 322 and available thereafter to any of the programmers connected to the network 320, including the programmer 312.

Figure 4:
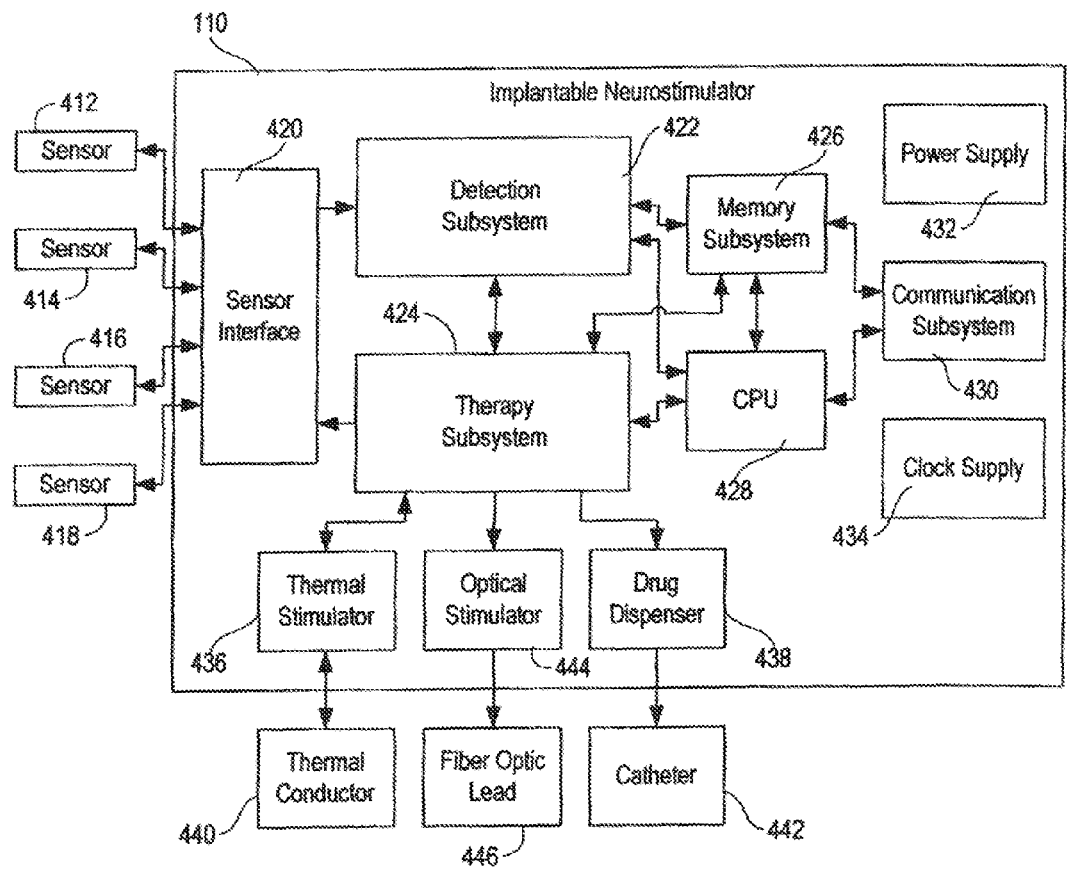
FIG. 4 is a block diagram illustrating the major functional subsystems of an implantable neurostimulator according to the invention.

FIG. 4 is an overall block diagram of the implantable neurostimulator device 110 used for measurement, detection, and treatment according to the invention. Inside the housing of the neurostimulator device 110 are several subsystems making up the device. The implantable neurostimulator device 110 is capable of being coupled to a plurality of sensors 412, 414, 416, and 418 (each of which may be individually or together connected to the implantable neurostimulator device 110 via one or more leads or which may communicate with the device via telemetry), which in an embodiment of the invention are electrodes used for both sensing and stimulation, or may include transducers and outputs for the delivery of other treatment modalities. In the illustrated embodiment, the coupling is accomplished through a lead connector.

Although four sensors are shown in FIG. 4, it should be recognized that any number is possible, and in an embodiment described in detail herein, eight electrodes are used as sensors. In fact, it is possible to employ an embodiment of the invention that uses a single lead with at least two electrodes, or two leads each with a single electrode (or with a second electrode provided by a conductive exterior portion of the housing in one embodiment), although bipolar sensing between two closely spaced electrodes on a lead is preferred to minimize common mode signals including noise. In an alternate embodiment of the invention, sensing and/or stimulation electrodes are used in combination with sensors, such as temperature and blood flow sensors, as will be described below.

The sensors 412, 414, 416 and 418 are in contact with the patient's brain or are otherwise advantageously located to receive signals (e.g., EEG) or provide electrical stimulation or another therapeutic modality (e.g., optical). In an embodiment of the invention, one or more of the sensors 412, 414, 416 and 418 can be a biosensor, an optical sensor, an electrochemical sensor, a temperature sensor, or any of a number of sensor types capable of measuring cerebral blood flow, oxygenation, oxygen utilization, or any other local physiological condition of interest. See U.S. Pat. No. 7,341,562 to Pless et al. for "Modulation and Analysis of Cerebral Perfusion in Epilepsy and Other Neurological Disorders," which is hereby incorporated by reference as though set forth in full herein.

Each of the sensors 412, 414, 416 and 418 is coupled to a sensor interface 420, either electrically or via telemetry. Preferably, the sensor interface is capable of selecting electrodes as required for sensing and stimulation; accordingly the sensor interface is coupled to a detection subsystem 422 and a therapy subsystem 424 (which, in various embodiments of the invention, may provide electrical stimulation and other therapies). The sensor interface 420 may also provide any other features, capabilities, or aspects, including but not limited to amplification, isolation, impedance measurement, and charge-balancing functions, that are required for a proper interface with neurological tissue and not provided by any other subsystem of the device 110.

In an embodiment of the invention in which electrical signals are received by electrodes and analyzed, the detection subsystem 422 includes and serves primarily as a waveform analyzer. It will be recognized that similar principles apply to the analysis of other types of waveforms received from other types of sensors. Detection is generally accomplished in conjunction with a central processing unit (CPU) 428. The waveform analyzer function of the detection subsystem 422 is adapted to receive signals from the sensors 412, 414, 416 and 418, through the sensor interface 420, and to process those signals to identify abnormal neurological activity characteristic or "signature" of a disease or symptom thereof. One way to implement such waveform analysis functionality is disclosed in detail in U.S. Pat. No. 6,016,449 to Fischell et al. for "System for Treatment of Neurological Disorders" issued Jan. 18, 2000, incorporated by reference above. Additional inventive methods are described in U.S. Pat. No. 6,810,285 to Pless et al. for "Seizure Sensing and Detection Using an Implantable Device" issued Oct. 26, 2004, of which relevant details will be set forth below (and which is also hereby incorporated by reference as though set forth in full). The detection subsystem may optionally also contain further sensing and detection capabilities, including but not limited to parameters derived from other physiological conditions (such as electrophysiological parameters, temperature, blood pressure, neurochemical concentration, etc.). In general, prior to analysis, the detection subsystem performs amplification, analog to digital conversion, and multiplexing functions on the signals in the sensing channels received from the sensors 412, 414, 416 and 418.

The therapy subsystem 424 is capable of applying electrical stimulation or other therapies to neurological tissue. This can be accomplished in any of a number of different manners. For example, it may be advantageous in some circumstances to provide stimulation in the form of a substantially continuous stream of pulses, or on a scheduled basis. In an embodiment of the invention, scheduled therapy (such as stimulation via biphasic pulses or other waveforms, such as low-frequency sine waves) can be performed by the device 110 in addition to and independent of responsive therapy. Preferably, therapeutic stimulation is provided in response to abnormal neurological events or conditions detected by the waveform analyzer function of the detection subsystem 422. As illustrated in FIG. 4, the therapy subsystem 424 and the signal analyzer function of the detection subsystem 422 are in communication; this facilitates the ability of therapy subsystem 424 to provide responsive electrical stimulation and other therapies, as well as an ability of the detection subsystem 422 to blank the amplifiers while electrical stimulation is being performed to minimize stimulation artifacts. It is contemplated that the parameters of a stimulation signal (e.g., frequency, duration, waveform) provided by the therapy subsystem 424 would be specified by other subsystems in the implantable device 110, as will be described in further detail below.

In accordance with the invention, the therapy subsystem 424 may also provide for other types of stimulation, besides electrical stimulation described above. In particular, in certain circumstances, it may be advantageous to provide audio, visual, or tactile signals to the patient, to provide somatosensory electrical stimulation to locations other than areas of the brain (e.g. sensory cortices), or to deliver a drug or other therapeutic agent (either alone or in conjunction with electrical stimulation). Any of these therapies can be provided in a non-responsive therapy modality, such as scheduled therapy, either alone or in combination with a responsive therapy regimen.

Also the implantable neurostimulator device 110 contains a memory subsystem 426 and the CPU 428, which can take the form of a microcontroller. The memory subsystem is coupled to the detection subsystem 422 (e.g., for receiving and storing data representative of sensed electrographic or other signals and evoked responses), the therapy subsystem 424 (e.g., for providing stimulation waveform parameters to the therapy subsystem for electrical stimulation), and the CPU 428, which can control the operation of (and store and retrieve data from) the memory subsystem 426. In addition to the memory subsystem 426, the CPU 428 is also connected to the detection subsystem 422 and the therapy subsystem 424 for direct control of those subsystems.

Also provided in the implantable neurostimulator device 110, and coupled to the memory subsystem 426 and the CPU 428, is a communication subsystem 430. The communication subsystem 430 enables communication between the device 110 and the outside world, particularly an external programmer 312 and a patient initiating device 324, both of which are described above with reference to FIG. 3. In an embodiment of the invention, described below, the communication subsystem 430 also facilitates communication with other implanted devices.

Several support components are present in the implantable neurostimulator device 10, including a power supply 432 and a clock supply 434. The power supply 432 supplies the voltages and currents necessary for each of the other subsystems. The clock supply 434 supplies substantially all of the other subsystems with any clock and timing signals necessary for their operation, including a real-time clock signal to coordinate programmed and scheduled actions and the timer functionality used by the detection subsystem 422 that is described in detail below.

In an embodiment of the invention, the therapy subsystem 424 is coupled to a thermal stimulator 436 and a drug dispenser 438, thereby enabling therapy modalities other than electrical stimulation. These additional treatment modalities will be discussed further below. The thermal stimulator 436 and the drug dispenser 438 are coupled to respective outputs, such as a thermal conductor/generator 440 and a catheter 442, positioned at a desired location. Any of the therapies delivered by the therapy subsystem 424 is delivered to a therapy output at a specific site; it will be recognized that the therapy output may be a stimulation electrode, a drug dispenser outlet, a magnetic stimulator, a transcranial magnetic stimulator, an optical stimulator, or a thermal stimulator (e.g., Peltier junction or thermocouple) as appropriate for the selected modality.

The therapy subsystem 424 is further coupled to an optical stimulator 444 and a fiber optic lead 446, enabling optical stimulation of neural structures in the brain, spinal cord, and nerves. Generally, the optical stimulator 444 includes a controllable light emitter (such as at least one LED or laser diode) that is situated onboard or in close proximity to the device 110, and the light is transmitted to the stimulation site via the fiber optic lead 446. Alternatively, the optical generator can be located at least partially external to the patient, with the fiber optic lead used to bring the light to the target region. One or more lenses may be used at the proximal or distal ends of the fiber optic lead 446, for example, to increase light collection from the emitter (at the proximal end) and to focus the optical stimulation (at the distal end). It is understood that optical stimulation intensity is a function of both wavelength and intensity; different patients and different targets will react differently to different light colors, intensities, stimulation pulse widths, and stimulation burst durations (where pulse trains are delivered).

It should be observed that while the memory subsystem 426 is illustrated in FIG. 4 as a separate functional subsystem, the other subsystems may also require various amounts of memory to perform the functions described above and others. Furthermore, while the implantable neurostimulator device 110 is preferably a single physical unit (i.e., a control module) contained within a single implantable physical enclosure, namely the housing described above, other embodiments of the invention might be configured differently. The neurostimulator 110 may be provided as an external unit not adapted for implantation, or it may comprise a plurality of spatially separate units each performing a subset of the capabilities described above, some or all of which might be external devices not suitable for implantation. A transcranial magnetic stimulator may be used and may provide responsive therapy by working in conjunction with implanted sensors. Also, it should be noted that the various functions and capabilities of the subsystems described above may be performed by electronic hardware, computer software (or firmware), or a combination thereof. The division of work between the CPU 428 and the other functional subsystems may also vary—the functional distinctions illustrated in FIG. 4 may not reflect the partitioning and integration of functions in a real-world system or method according to the invention.

Figure 1:
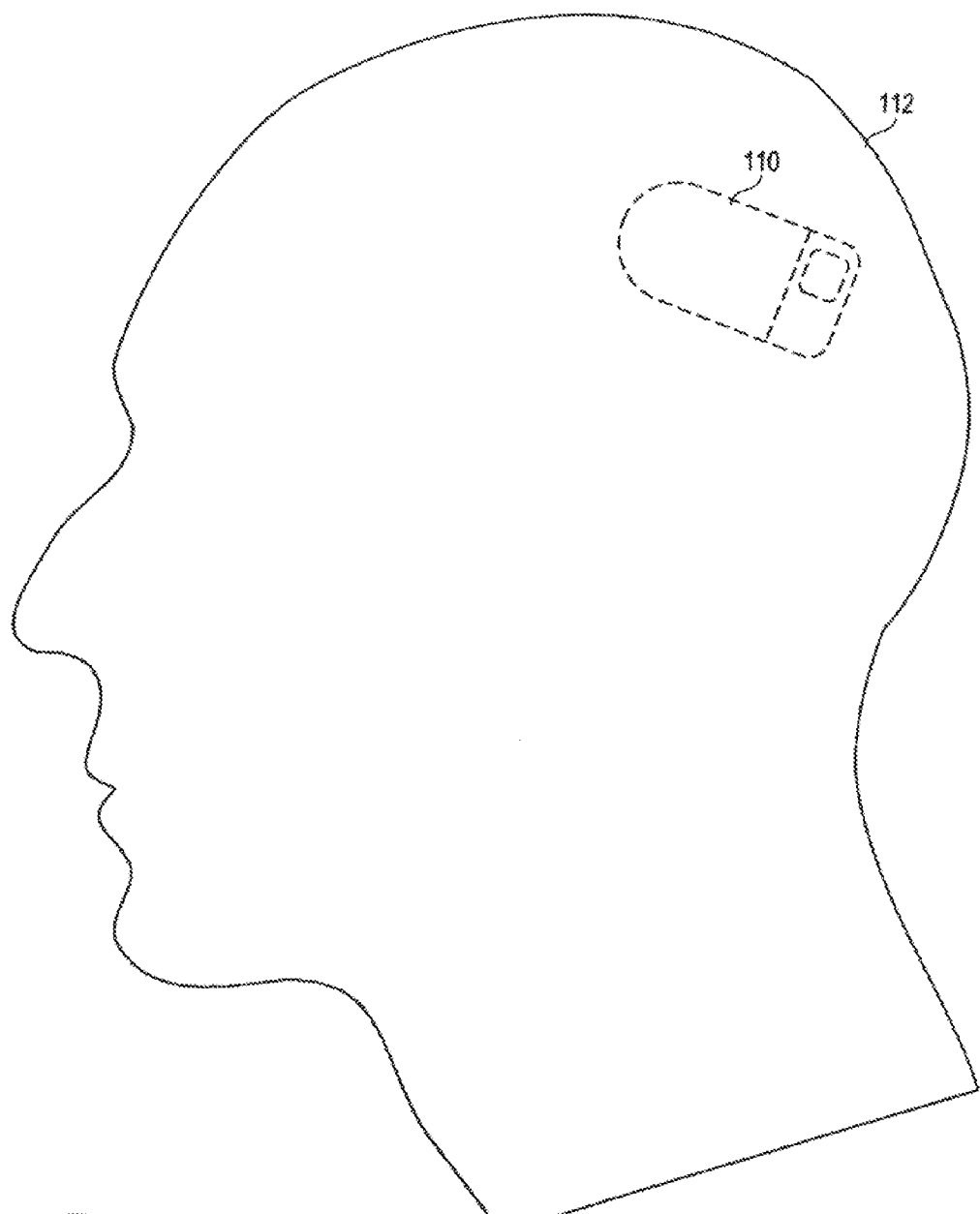
FIG. 1 is a schematic illustration of a patient's head showing the placement of an implantable neurostimulator according to an embodiment of the invention.
Figure 5:
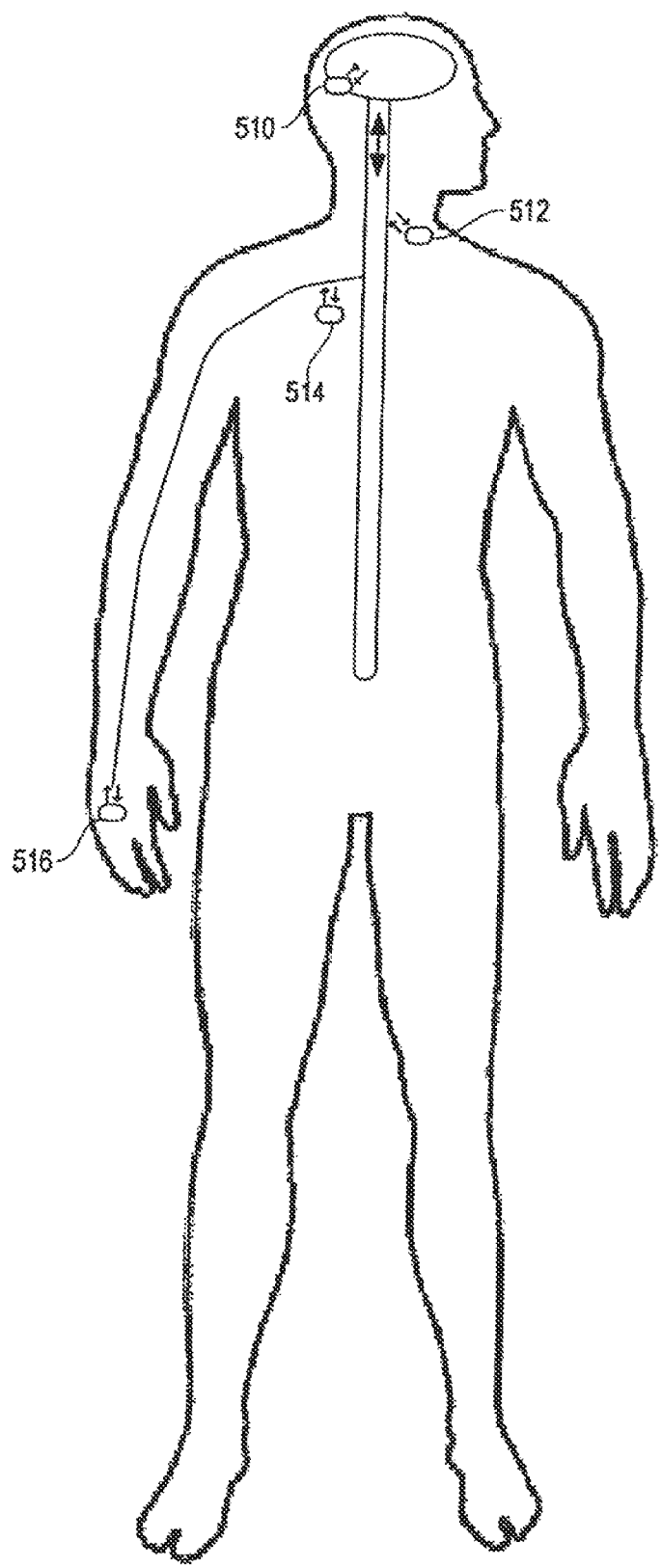
FIG. 5 is a schematic representation of a human patient with multiple interconnected implantable neurostimulator devices in an embodiment of the invention.

In an embodiment of the invention, multiple implanted and coordinated modules are employed to treat pain at multiple sites. This embodiment is illustrated in FIG. 5. In the illustration, a first implanted module 510 is located in the patient's cranium (as shown in FIGS. 1-2) and is configured to provide deep brain and/or cortical, and continuous and/or responsive, stimulation according to the invention. Additional modules may be used to augment therapeutic benefit of stimulation. For example, in one embodiment a second implanted module 512 is implanted in tissue near the patient's spinal column, a third implanted module 514 is implanted in tissue near a proximal end of a peripheral nerve, and a fourth implanted module 516 is implanted in tissue near a distal end of a peripheral nerve. In practice, two or more implanted modules can be coordinated according to the invention. Such coordinated therapy can entail stimulating jointly to decrease unwanted symptoms, or stimulating at different locations to treat different symptoms, and/or stimulating at different locations based upon the signatures detected by evaluation of sensed signals.

Figure 6:
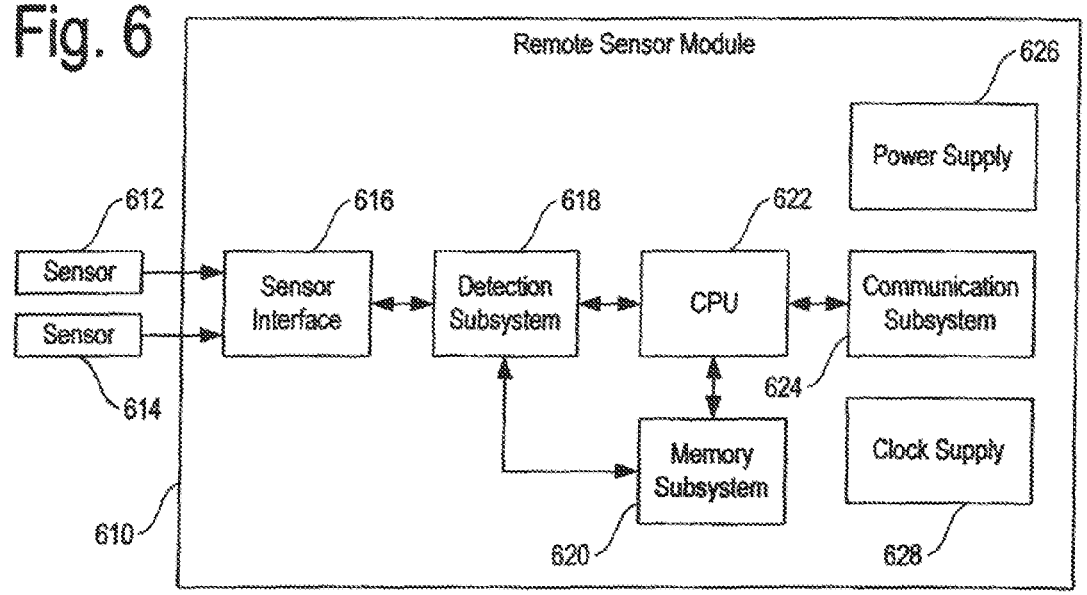
FIG. 6 is a block diagram illustrating the major functional subsystems of a remote sensing module according to the invention.
Figure 7:
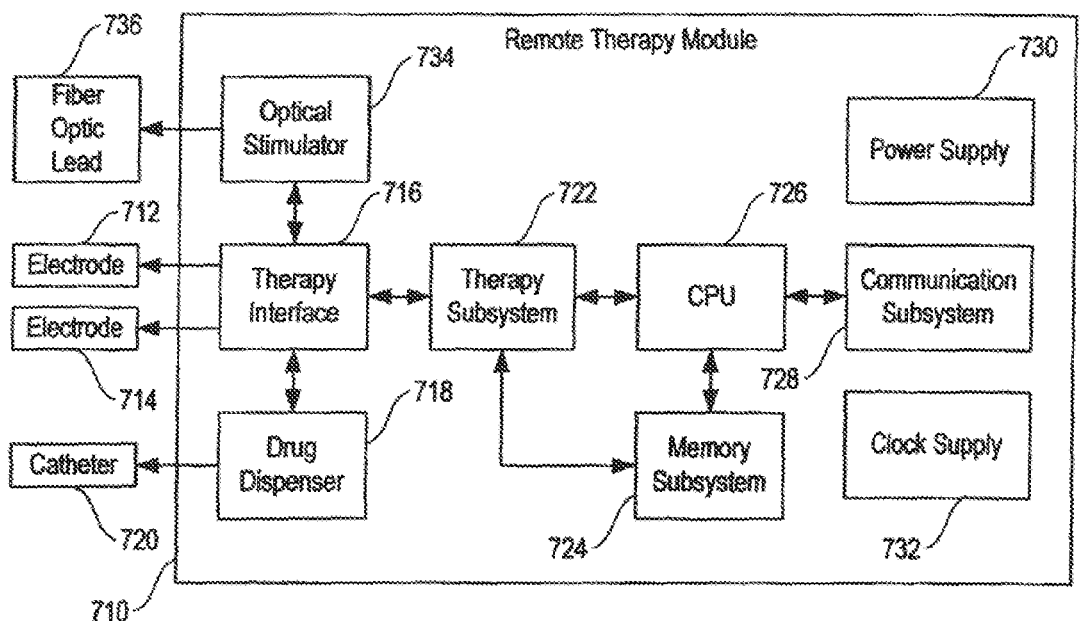
FIG. 7 is a block diagram illustrating the major functional subsystems of a remote therapy module according to the invention.

In the disclosed embodiment, the first implanted module 510 is a master device, coordinating the actions of the remaining modules. Each of the second, third, and fourth modules 512, 514 and 516 in an embodiment of the invention may comprise a duplicate of the master device but configured to receive coordination commands from the master device 510, or may comprise a remote sensor module (as illustrated in FIG. 6) or a remote therapy module (as illustrated in FIG. 7). The second implanted module 512 may be configured primarily as a sensor to receive signals from one or more locations of the spinal column, provide coordinated spinal cord stimulation (SCS), or both. The third implanted module 514 may be configured to receive signals from the peripheral nerve, provide coordinate peripheral nerve stimulation (PNS), or both.

The fourth implanted module 516 may be configured to receive signals from a more distal section of the peripheral nerve or other nearby physiological indicators, provide PNS, or both. Consequently then, with multiple implanted modules according to the invention, brain stimulation, spinal cord stimulation, and peripheral nerve stimulation can be delivered and employed in a coordinated treatment regimen to provide the best possible pain relief to the patient, relieving sensory, affective, and cognitive components of the pain. The multiple implanted modulates can each provide sensing and stimulation for single or multiple modalities.

As set forth above, sensing of signals according to the invention may be performed in one or more bilateral or unilateral locations of the patient's primary somatosensory cortex (SI), secondary somatosensory cortex (SII), anterior cingulate cortex, prefrontal cortex, anterior insular cortex, thalamus, sensory thalamus, spinal cord, and peripheral nerves. Certain types of endogenous activity signatures from the SI area are believed correlated primarily with the sensory component of pain, facilitating localization of pain. The SII area, cingulate cortex, prefrontal cortex, and insular cortex are primarily associated with the affective component, with the cingulate cortex also particularly involved in the cognitive and psychological aspects of pain processing. The thalamus is involved in both sensory and affective components, as it serves as a central mediating structure for pain perception (e.g. sensory gating). The spinal cord and peripheral nerves are involved in the transmission of pain signals from the peripheral nervous system to the brain, and hence are implicated in nearly all nociceptive and neuropathic pain processing. In some cases, abnormal activity may also be observed in the striatum, cerebellum, and supplementary motor area. In general, it is not known whether activity in these areas reflects the nervous system receiving and processing pain or an attempt to modulate the pain through descending inhibitory mechanisms. It should be noted that other structures not listed may also play a role in both normal and pathological pain processing and perception.

Treatment may be performed to modulate one or more of the thalamus, motor cortex, brain stem, periaqueductal gray (PAG), periventricular gray (PVG), precentral gyms, parietal cortex, spinal cord, and peripheral nerves. The PAG area, in particular, is part of the midbrain and is postulated to be a central point of control for the affective component of pain in the cortex. Localized stimulation in the motor cortex tends to regulate the sensory component. Other structures, including some not specifically listed, may modulate sensory and/or affective components in various proportions. These structures may be identified by clinical observations, noting response to different drug interventions, patient histories, and by various neuroimaging methods which can be performed in conjunction with sensory stimulation, tasks, and interventions. The structures can also be identified during the implantation procedure based upon electrophysiological or neurochemical signatures which reflect abnormal levels or patterns of basal or evoked activity. The mechanism of action is believed to be consistent with the "gate control" theory of pain as described above.

In an embodiment of the invention, as illustrated in FIG. 5, a device is positioned relatively near each anatomic structure sought to be a source of information or a target of treatment. Positioning devices near structures of interest allows shorter leads to be used between devices and their sensors, thereby reducing the risk of mechanical failure and also reducing surgery complexity and scope.

Several exemplary clinical scenarios are set forth below.

For central pain, it has been found that regular oscillatory signals observable in the sensory thalamus may correlate with pain treatable by stimulation in the periventricular gray (PVG). See, e.g., D. Nandi et al., "Thalamic field potentials in chronic central pain treated by periventricular gray stimulation—a series of eight cases," *Pain* 101 (2003) 97-107. Accordingly, then, in an embodiment of the invention, a cranially implanted device is tuned to identify ECoG activity primarily in the range of 0.1 to 1.0 Hz (most such observed activity falls in the range of 0.2-0.4 Hz). In particular, a device 110 may use an analog or digital band-pass filter and integrator, or a half wave detection tool (with a relatively high hysteresis value as described below) to specifically identify/measure high-amplitude activity in the frequency range of interest and ignore normal higher frequency activity; the oscillation frequency is generally a patient-specific determination. Alternatively, an area-based detection tool (also described below) may also be used.

When spectral analyses are applied to sensed signals, the duration of windowed data becomes an issue in connection with frequency resolution. By way of example, in order to obtain estimates of spectral energy spanning 0.2 Hz, the data must be collected in at least 5 second sample windows. While signal processing methods such as zero-tapering, wavelet decomposition, and moving averages may be used to shorten this effective sampling window, these may be prone to spectral leakage, in that energy at nearby frequencies may leak into the band which is being measured. Accordingly, in one embodiment, assessment of stimulation will require evaluation of signals as these are assessed in approximately 4 to 10 second samples. A mean and standard deviation can be calculated upon a specified number of samples prior to stimulation, and stimulation can be guided in order to produce a statistically significant reduction in spectral power within a specified 0.2 Hz band. The band may be chosen by comparing an individual's demographic data to that of an age and sex matched normative data set collected either during pain or in the absence of pain. The spectral band can also be chosen based upon a self-norm where activity is measured during pain and in the absence of pain, or by comparing activity within region or spectral band to activity in a different region of a patient, or in a different band of spectral power. In other words, the spectral estimate can be an absolute or relative measure such as Delta 1 power, relative Delta 1 power (i.e. divided by total power) or Delta1/Delta2 ratio. The center frequency of the measured band as well as its width can be determined in a number of manners such as looking at the shape, variance, and covariance of spectral energy within the computed EEG spectra.

Another alternative is to use one or more analog or digital band-pass filters which are tuned to at least one frequency range of interest in order to capture the neurophysiological signature of the pain symptom. For instance, a bandpass filter can be used which passes spectral energy between 0.2 Hz and 0.4 Hz. This would be appropriate when the peak of spectral energy related to the pain signal occurred at about 0.3 Hz, and was narrow band. However, physiological signals often deviate in their center frequency over time, and therefore while often having a center frequency of 0.3 Hz, the peak energy could occur at 0.4 or 0.45 Hz which would be outside of the range of the filter. Accordingly, using a small bank of band-pass filters permits the measurement of power even when the peak frequency fluctuates somewhat over time.

One method for responsively treating pain with an implantable device includes sensing a signal from an implanted sensor (for example, a sensor in the thalamus), analyzing the signal to detect a pain signature in the signal, and providing stimulation when this is detected. In one embodiment, one or more bands of narrow band power within a specified range are measured and a pain signature is detected when selected spectral energy meets a specified criterion. For example, 10 narrow band-pass filters, each having center frequencies separated by 0.2 Hz, and ranging from 0.5 and 2.5 Hz, can be implemented to provide continuous estimates of narrow band spectral power over that frequency range. In order to track the pain signal, the filter having the maximum spectral power can be selected and, if the power is above a specified level, then a pain signature is detected. Alternatively, spectral power may always be measured in the same narrow band-frequency. The power may be compared to a specified threshold, a self-norm, spectral power at other frequencies, or spectral power at other sensors. For example, when sensors are located to sense from regions of the somatosensory cortex, the EEG for an electrode located more proximal to a region experiencing pain (EEGp) can be compared to the EEG of neighboring electrodes (EEGn) in order to detect a relevant pain signature (e.g., spectral power of selected bands of EEGp/EEGn, or coherence computed between EEGp and EEGn which may be compared to coherence computed between one or more spectral bands of two or more EEGn's).

It would be particularly advantageous to implant a lead with electrodes in the thalamus (specifically the ventroposterolateral thalamic nucleus, or VPL) and observe the particular spectral changes which occur as the patient experiences pain and pain relief, such as an increase or decrease of power within at least one frequency band. Alternatively, or additionally, methods of pattern or waveform recognition may be used to detect and measure physiological signatures associated with symptoms of the pain disorder. Further, both increases and decreases in power, across different bands, may be representative of a pain signature (Sarnthein J, Stern J, Aufenberg C, Rousson V, Jeanmonod D. Increased EEG power and slowed dominant frequency in patients with neurogenic pain. *Brain*. 2006 January; 129(Pt 1):55-64, incorporated by reference herein), as can increases in coherence (Drewes A M, Sami S A, Dimcevski G, Nielsen K D, Funch-Jensen P, Valeriani M, Arendt-Nielsen L. Cerebral processing of painful oesophageal stimulation. A study based on independent component analysis of the EEG. *Gut*. 2005), and changes in measures of complexity/chaos. These deviations from the values that occur in normative data can be evaluated by multivariate equations to produce scores reflective of the pain. Such a measure could be the Mahalanobis Distance of selected spectral regions compared to a self or population norm. Generally, concurrently and in a single surgery session, a therapy lead would be implanted in the PVG, at least one implantable module would be implanted and connected to the leads, and subsequently the patient's wounds would be closed. Following surgery, all further programming and tuning of the device can be accomplished via data telemetry.

Stimulation, generally occurring as charge-balanced biphasic waveforms (pulsatile or non-pulsatile waveforms, as described below), is then applied to the PVG in response to observed thalamic oscillations. In addition to suppressing the patient's symptoms, this also results in the suppression of the thalamic oscillations. Effective stimulation frequencies have been found to range from 5 to 35 Hz; for purposes of this disclosure, it is believed that stimulation (e.g., using pulsatile or non-pulsatile modulations, repetitions, rates or frequencies) from 0.2 to 200 Hz may be effective in various patients. Different stimulation frequencies may be selected according to the invention and applied while activity in the thalamus continues to be observed; stimulation frequencies that best suppress the thalamic oscillations determined to be signatures of (i.e., correlated with) the pain symptoms are considered to be the most effective stimulation frequencies for pain relief as well.

The duration of pain relief and of the suppression of low-frequency thalamic activity has been found to extend 5-15 minutes, and potentially longer, past the application of therapeutic stimulation. Accordingly, then, a system according to the invention is programmed to apply an interval of stimulation upon the observation of a pain signature such as a low frequency thalamic oscillation exceeding a programmed amplitude threshold. The duration of the therapy interval may depend on a timing strategy that is found via clinical observation to be best for the particular patient, or may be related to the observed amplitude of thalamic oscillations or one or more other factors. In one treatment mode, after stimulation is applied, the system continues to sense data signals and to look for thalamic oscillations and will re-apply stimulation when the amplitude threshold is again exceeded.

In an embodiment of the invention, the level of stimulation provided to the PVG (or the motor cortex, or other neural tissue) is modulated by a characteristic of observed thalamic oscillations such as amplitude, duration, frequency, or time since prior occurrence. Accordingly, then, after signals are detected, and while they are ongoing, the level of therapy (including possible changes to stimulation amplitude, pulse width, or frequency) applied is controlled to minimize the observed oscillations (and the patient's corresponding symptoms of pain). The correlation between stimulation level and observed magnitude of the pain signature is not necessarily linear; some patient-specific clinical observation and measurement or real-time feedback control of the therapy subsystem 424 is recommended.

It will be appreciated that the foregoing exemplary treatment strategy may only treat part of the pain, e.g. the affective component of central pain. Accordingly, it may also be effective to provide other stimulation in connection with the PVG stimulation to treat additional components or to provide further relief in the same components. For example, motor cortex stimulation in or near the portion of the cortex responsible for the portion of the body where pain is experienced may also be stimulated. This stimulation may be provided in a manner that is responsive to the same signatures as the PVG stimulation (i.e., certain types or frequencies of thalamic oscillations), it may be responsive to a different condition as described elsewhere in this description, or it may be provided continuously, intermittently, or on a timed program. Multiple stimulation electrodes can be used to cover a larger portion of the motor cortex if it is deemed clinically advantageous.

In cases of severe chronic nociceptive pain, such as cancer pain, arthritis pain, or post-surgical pain, an embodiment of the invention using at least two modules (a centrally implanted master device module and a remote peripherally-located sensor module, though in an alternative embodiment of the invention a single module can be used) senses activity in the patient's peripheral nerves and provides electrical stimulation therapy to the brain in the thalamus, periaqueductal gray matter, periventricular gray matter, and/or motor cortex. The central (e.g., cranially implanted) master device is coupled via leads and electrodes to the stimulation sites in the brain. The remote sensor module receives signals from one or more nerves near the source of the pain to detect abnormal activity. In practice, abnormal activity in the peripheral nervous system is in many cases represented by a change in the frequency of spikes or impulses observed therein. Large fibers are approximately 3-20 micrometers (μm) in diameter so it is generally practical to measure aggregate activity from nerve bundles, or in an embodiment, individual or small numbers of action potentials using a microelectrode.

In cases of phantom limb pain, one or two modules are used to sense signals in the brain and spinal cord. In an embodiment of the invention, pain signatures are the abnormal activity representative of activation in the primary somatosensory cortex. This activity is measured and stimulation is responsively provided to the periaqueductal or periventricular gray matter and the motor cortex.

Allodynia, a hypersensitivity to innocuous stimuli (light touch, drafts, etc.) often present in central pain, has some unique characteristics not often observed in other forms of chronic pain. In particular, a decrease in activation and cerebral blood flow is often observed in the cingulate gyms. This activity can be measured by the invention, by sensing electrical activity related to reduced activation (and hence reduced signal levels and complexity as may be measured by the waveform analyzer and reflected, for example, in reduced magnitude of higher frequency spectral components, or reflected in Hjorth parameters of a periodogram including first and second derivatives of selected bands) or direct measurement of cerebral blood flow by temperature, optical, or plethysmographic means. Such activity is also correlated with increased activity in the thalamus, insular cortex, and secondary somatosensory area. Stimulation may be applied to the thalamus or periaqueductal/periventricular gray and may be adjusted or initiated responsively to the sensed pain signatures.

Dysesthesia, a burning sensation present in central pain, is subject to slow summation. That is, the intensity of the pain is correlated with its duration, and the pain tends to build up over time. Accordingly, detection and treatment of the invention, on a selective and intermittent basis, is particularly advantageous, particularly when both sensory and affective components are targeted. Dysesthesia is modulated, in an embodiment of the invention, by monitoring activity in the secondary somatosensory cortex, cingulate gyms, prefrontal cortex, and/or insular cortex, and applying responsive therapy to the thalamus, periaqueductal gray matter, periventricular gray matter, precentral gyms, and as necessary in the cingulate gyms to control the cognitive component of the pain.

Tinnitus, recognized by some researchers to be a form of chronic pain, can be sensed in the patient's auditory cortex, cingulate gyms, and other brain structures associated with affective pain. Inappropriate sensed activity may be terminated by applying responsive, intermittent therapy to the auditory cortex, brainstem, or thalamus or/and other deep brain structures and their ascending pathways.

The foregoing scenarios are considered illustrative but are not limiting.

Considered more generally, it has been observed that pain symptoms frequently correlate with abnormal activation patterns in various parts of the patient's brain. Imaging techniques such as magnetic resonance imaging (MRI) can identify structural abnormalities, and functional MRI (fMRI), positron emission tomography (PET), single photon emission computed tomography (SPECT), and various forms of neurospectroscopy including magnetic resonance spectroscopy (MRS), near infrared spectroscopy (NIRS), and proton neurospectroscopy can be used to identify activation patterns and target those areas according to the invention for either sensing (which may be deployed to measure cerebral blood flow or oxygenation, or more typically is electrographic in nature) or therapy. Patient-specific template generation on the basis of collected electrographic (and other sensor signal) data, as described above, would be used to "tune" the detection capabilities of the device to a patient's specific detection needs, define signatures of the patient's pain, and provide mapping of the physiological measurements onto their related symptoms in order to determine the physiological changes that correspond to symptoms such as the magnitude of subjective pain.

With regard to treatment options outside of the guidelines and scenarios set forth above, clinical experience on a patient-by-patient basis provides guidance as to whether activating or inhibiting a target location may provide relief to the patient, and trends may be observed over populations of patients having similar symptoms and reactions to therapy according to the invention.

Effective treatment of pain according to the present invention may, over the course of time and through the effects of neuroplasticity, cause the patient's nervous system to eventually "unlearn" its dysfunctional patterns in central pain, and stimulation may be discontinued with no resumption in symptoms.

Returning now to the components of a system according to the invention, an exemplary remote sensor module 610 according to the invention is illustrated in FIG. 6. In the disclosed embodiment, the remote sensor module 610 includes a number of the same subsystems found in a master implantable device such as the device 110. Specifically, as disclosed, two sensors 612 and 614 (which may be electrodes or other types of sensors as described elsewhere in this document) are coupled to a sensor interface 616, which in turn is coupled to a detection subsystem 618. In addition to detecting characteristics of the sensed signal related to pain, the detection subsystem 618 can also function to classify the sensed signals, or can provide a score or index based upon signal processing of the one or more signals detected at each sensor. Signal processing can include, for example, filtering, pattern recognition, peak detection, spectral and period analysis, regression, prediction, and classification schemes related to evaluating the sensed signal and selecting appropriate responsive neurostimulation treatment parameters. The detection subsystem 618 can also be used to generate or modify the stimulation therapy using control laws, which may comprise one or more linear or non-linear transfer functions, may contain step functions, may be altered based upon evaluation of one or more characteristics of the sensed signal. The detection subsystem 618 can obtain reference values from the memory subsystem 620 related to self-norms, and can store results of its operations in the memory subsystem for later reference. Although two sensors are shown for simplicity of illustration (and a potentially advantageous reduction in complexity), any number would be possible in a remote sensor module according to the invention. The remote sensor module 610 also includes a memory subsystem 620, a CPU 622, a communication subsystem 624, a power supply 626, and a clock supply 628. The components of the remote sensor module 610 perform generally the same functions as the corresponding components of the fully featured implantable device 110 (FIG. 4), but the CPU 622 is specifically configured to operate the remote sensor module 610 in conjunction and in a coordinated fashion with the device 110.

Preferably, and consistent with the description set forth above, the remote sensor module 610 is capable of performing event detection independently from other devices, and rather than applying therapy directly, communicating information representative of event detection via the communication subsystem 624 to the device 110, thereby facilitating inter-device coordination. The coordination process will be described in further detail below.

An exemplary remote therapy module 710 according to the invention is illustrated in FIG. 7. As with the remote sensor module 610 (FIG. 6), the remote therapy module 710 shares components and subsystems with the fully featured implantable device 110 (FIG. 4), and like-named components serve similar functions. Accordingly, then, the illustrated embodiment of the remote therapy module 710 includes two electrodes 712 and 714 coupled to a therapy interface 716. The therapy interface 716 is also coupled to a drug dispenser 718, which may be disposed within the remote therapy module 710 or alternatively positioned elsewhere for ease in refilling one or more drug reservoirs within the dispenser 718. In either case, the drug dispenser 718 is coupled to a catheter 720 with its distal end positioned at an advantageous location for therapy, which may be either in the central nervous system or peripherally. The remote therapy module 710 also includes a therapy subsystem 722, a memory subsystem 724, a CPU 726, a communication subsystem 728, a power supply 730, and a clock supply 732.

As described above, the remote therapy module 710 is equipped with an optical stimulator 734 and a fiber optic lead 736, enabling optical stimulation of neural structures in the brain, spinal cord, and nerves. Alternatively, the optical stimulator 734 can simply serve to route optical signals generated externally to the remote therapy module 710, but which are fed into the unit. Alternatively, due to issues of power consumption and storage space, the entire optical stimulator 734 can be a separate module.

The remote therapy module 710 is configured to receive commands from a master device such as the device 110 (FIG. 4). Accordingly, it has no sensing and detection capabilities of its own; rather, it is driven by commands and scheduling information received from the master device via the communication subsystem 728. Commands relating to responsive therapies are typically provided in real time, whereas therapy schedules may be communicated in advance and stored by the remote therapy module 710. As will be described below, this enables coordination between any master device and remote therapy modules according to the invention. Alternatively, the remote therapy module 710 is configured to work alone, or in combination with a master device 110, but no communication subsystem 728 is present and coordinated stimulation occurs merely due to the real-time clock 732.

It is possible for remote modules to be activated and deactivated by the master device, thereby saving energy. For example, in one embodiment of the invention, a remote sensor module can be activated (i.e., brought out of a "sleep" mode) by a signal from its communication subsystem. The continuously enabled sleep mode is a default low-power mode in which the modules can still receive commands from the master device 110. Only when the master neurostimulator device 110 identifies a potential condition that requires corroboration from the remote module, does it send a command to bring it out of sleep mode. That condition is either confirmed, ruled out, or responded to, and the remote module is subsequently returned to a "sleep" mode. This mode of operation will be described in further detail below. It is also possible that the energy requirements of sleep mode can be further decreased by having the remote modules "wake up" periodically (e.g., every 10 minutes) and communicate with the master device and determine if there is a potential condition that requires corroboration.

It will be recognized that a system according to the invention employing multiple modules capitalizes on an improved ability to sense signals in one portion of the patient's body and deliver therapy elsewhere. This is facilitated by the use of remote modules as described above, but the use of such modules is not necessary. It is possible to use a single device in an embodiment of the invention, with multiple leads to reach multiple detection and therapy targets in the body. However, remote modules do facilitate combination therapies, with stimulation and drugs being used in different areas to maximum effect.

Figure 8:
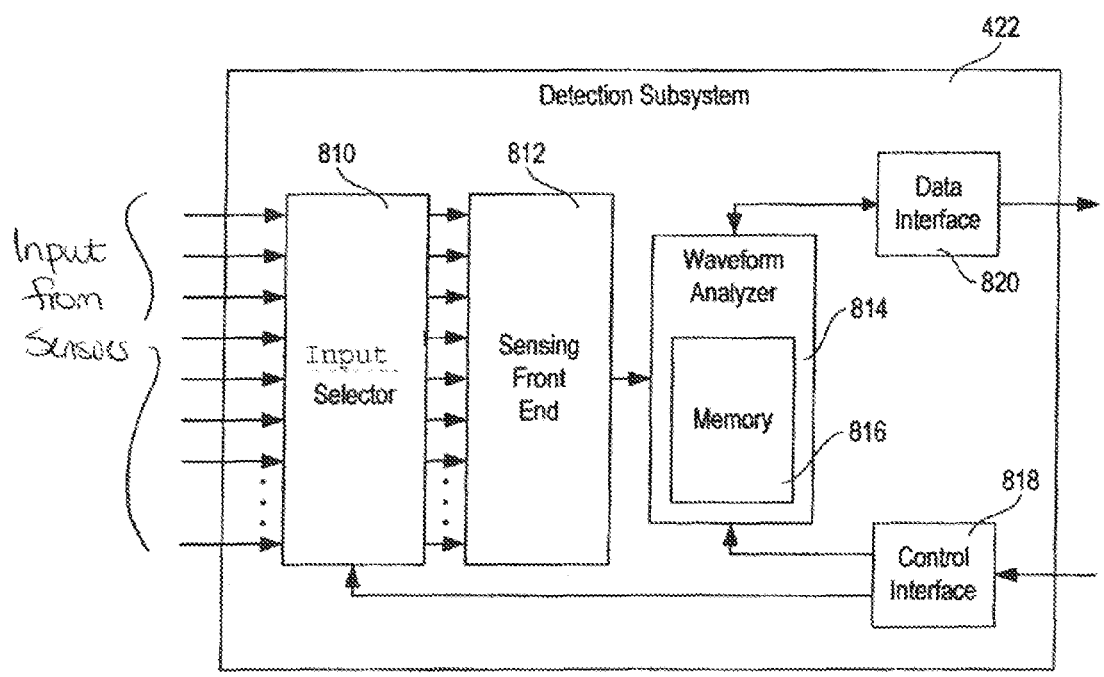
FIG. 8 is a block diagram illustrating the functional components of the detection subsystem of the implantable neurostimulator shown in FIG. 4.

FIG. 8 illustrates details of the detection subsystem 422 (FIG. 4). Inputs from the sensors 412, 414, 416 and 418 are on the left, and connections to other subsystems are on the right. It should also be noted that the description of the detection subsystem illustrated in FIG. 8 also applies to the detection subsystem 422 of FIGS. 4 and 618 of FIG. 6, with appropriate changes as necessary in a remote sensor module 610 as would be appreciated by a practitioner of ordinary skill in the art.

Signals received from the sensors 412, 414, 416 and 418 (as routed through the sensor interface 420) are received in an input selector 810. The input selector 810 allows the device to select which electrodes or other sensors (of the sensors 412, 414, 416 and 418) should be routed to which individual sensing channels of the detection subsystem 422, based on commands received through a control interface 818 from the memory subsystem 426 or the CPU 428 (FIG. 4). Preferably, when electrodes are used for sensing, each sensing channel of the detection subsystem 422 receives a bipolar signal representative of the difference in electrical potential between two selectable electrodes. Accordingly, the input selector 810 provides signals corresponding to each pair of selected electrodes to a sensing front end 812, which performs amplification, analog to digital conversion, and multiplexing functions on the signals in the sensing channels. When each electrode or sensor has two or more selectable contacts, each of which can communicate independently with the device 110 via the input selector, then the difference between contacts rather than electrodes may be measured.

A multiplexed input signal representative of all active sensing channels is then fed from the sensing front end 812 to a waveform analyzer 814. The waveform analyzer 814 is preferably a special-purpose digital signal processor (DSP) adapted for use with the invention, or in an alternative embodiment, may comprise a programmable general-purpose DSP. It may also have specialized analog circuitry such as filters, control circuitry, and circuitry for creating stimulation waveforms from the sensed signal using control laws. In the disclosed embodiment, the waveform analyzer has its own scratchpad memory area 816 used for local storage of data and program variables when signal processing or statistics are being performed. In either case, the signal processor performs suitable measurement, classification, and detection methods described generally above and in greater detail below. Any results from such methods, as well as any digitized signals intended for storage, analyses, control, or transmission to external equipment, are passed to various other subsystems of the device 110, including the memory subsystem 426 and the CPU 428 (FIG. 4) through a data interface 820. Similarly, the control interface 818 allows the waveform analyzer 814 and the input selector 810 to be in communication with the CPU 428. The waveform analyzer 814 is illustrated in detail in FIG. 10.

In one embodiment, the inputs from the sensors 412, 414, 416 and 418 receive signals from different sensors located to sense from different locations which are either related to the sensation of pain (Sp) or mostly not related to, or affected by, the sensation of pain (Sn). Sp and Sn may be two or more regions of the somatosensory cortex, may be in a structure such as the thalamus, may be contra-lateral structures, and/or may be located in two different brain structures. The characteristics of the pain signature sensed from the Sp region may be compared to a specified threshold, a self-norm, spectral power at other frequencies, or spectral power of signals obtained by other sensors that sense at non-pathological regions (Sn) of the cortex or regions of the thalamus or other brain structures. For example, when sensors are located to sense from several regions of the somatosensory cortex, the EEG for an electrode located more proximal to a region related to pain perception (EEGp) can be compared to the EEG of neighboring electrodes (EEGn) in order to detect a relevant pain signature. The ratio of spectral power of selected bands of the EEGp and EEGn signals could be used. Alternatively, coherence computed between EEGp and EEGn can be compared to coherence of one or more spectral bands computed for two or more EEGn's. The signal from the Sp region can, itself, be used to compute an index or score using either linear or non-linear measurement schemes, so that this value reflects a pain signature related to a neurophysiological or behavioral symptom of the pain. Alternatively, the signal from the Sp region can be compared to the signals from the Sn regions in order detect a pain signature, as may occur when a specific difference is found between the signals sensed from the Sp and Sn regions. The sensed signals can be obtained from ongoing activity of the brain or can be obtained in a time period immediately following stimulation either at the same location as the sensor or at a different location (i.e., the signals can be an evoked response to applied electrical, sensory, or other type of stimulation). In order to reduce computational needs, each of the signals can be routed to one or more analog or digital filters. The filters can be arranged in parallel in order to obtain several spectral estimates from the same signal, or can be arranged in series with routing to the ADC at different stages of filtering. Various combinations of filtering schemes will provide different advantages as is known to those skilled in the art. The filter characteristics can be pre-set or can be changed according to the subject's profile. For example, in order to easily obtain an estimate of an oscillation related to a pain symptom, the EEG signals from Sp and Sn regions can each be filtered by a narrow band filter and then integrated. The relative power between the two signals can be compared in order to derive the pain signature.

Figure 9:
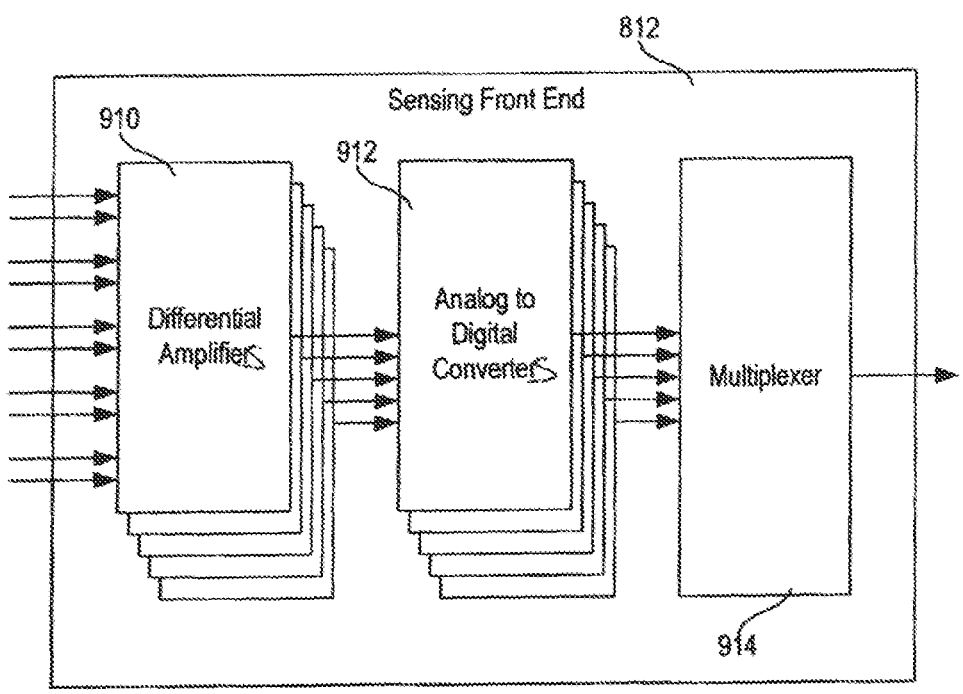
FIG. 9 is a block diagram illustrating the functional components of the sensing front end of the detection subsystem of FIG. 8.

Referring now to FIG. 9, the sensing front end 812 (FIG. 8) is illustrated in further detail. As shown, the sensing front end includes a plurality of differential amplifier channels 910, each of which receives a selected pair of inputs from the electrode selector 810. In a preferred embodiment of the invention, each of the differential amplifier channels 910 is adapted to receive or to share inputs with one or more other differential amplifier channels 910 without adversely affecting the sensing and detection capabilities of a system according to the invention. Specifically, in an embodiment of the invention, there are at least eight electrodes, which can be mapped separately to eight differential amplifier channels 910 representing eight different sensing channels and capable of individually processing eight bipolar signals, each of which represents an electrical potential difference between two monopolar input signals received from the electrodes and applied to the sensing channels via the electrode selector 810. For clarity, only five channels are illustrated in FIG. 9, but it should be noted that any practical number of sensing channels may be employed in a system according to the invention.

As set forth above, activity of interest occurs primarily above 0.1-0.2 Hz. Accordingly, the amplifier channels illustrated above can be equipped with high-pass filters to reject lower-frequency activity and DC signal components that might otherwise confound the detection capabilities of a system according to the invention. More than one stage of filtering and amplification may take place within each differential amplifier channel. Preferably, each amplifier is equipped with at least one band-pass filter and more preferably both filter and gain settings of the amplifier are programmable.

Each differential amplifier channel 910 feeds a corresponding analog to digital converter (ADC) 912. Preferably, the analog to digital converters 912 are separately programmable with respect to sample rates—in the disclosed embodiment, the ADCs 912 convert analog signals into 10-bit unsigned integer digital data streams at a sample rate selectable between 250 Hz and 500 Hz. In several of the illustrations described below where waveforms are shown, sample rates of 250 Hz are typically used for simplicity. However, the invention shall not be deemed to be so limited, and numerous sample rate and resolution options are possible, with tradeoffs known to individuals of ordinary skill in the art of electronic signal processing. When measuring signals having power at less than 1 Hz, even a sampling rate of 50 Hz is more than sufficient. The resulting digital signals are received by a multiplexer 914 that creates a single interleaved digital data stream representative of the data from all active sensing channels. As will be described in further detail below, not all of the sensing channels need to be used at one time, and it may in fact be advantageous in certain circumstances to deactivate certain sensing channels to reduce the power consumed by a system according to the invention.

It should be noted that as illustrated and described herein, a "sensing channel" is not necessarily a single physical or functional item that can be identified in any illustration. Rather, a sensing channel is formed from the functional sequence of operations described herein, and particularly represents a single electrical signal received from any pair or combination of electrodes, as preprocessed by a system according to the invention, in both analog and digital forms. See, e.g., U.S. Pat. No. 6,473,639 to Fischell et al. for "Neurological Event Detection Procedure Using Processed Display Channel Based Algorithms and Devices Incorporating These Procedures" issued Oct. 29, 2002, which is hereby incorporated by reference as though set forth in full herein. At times (particularly after the multiplexer 914), multiple sensing channels are processed by the same physical and functional components of the system; notwithstanding that, it should be recognized that unless the description herein indicates to the contrary, a system according to the invention processes, handles, and treats each sensing channel independently.

Figure 10:
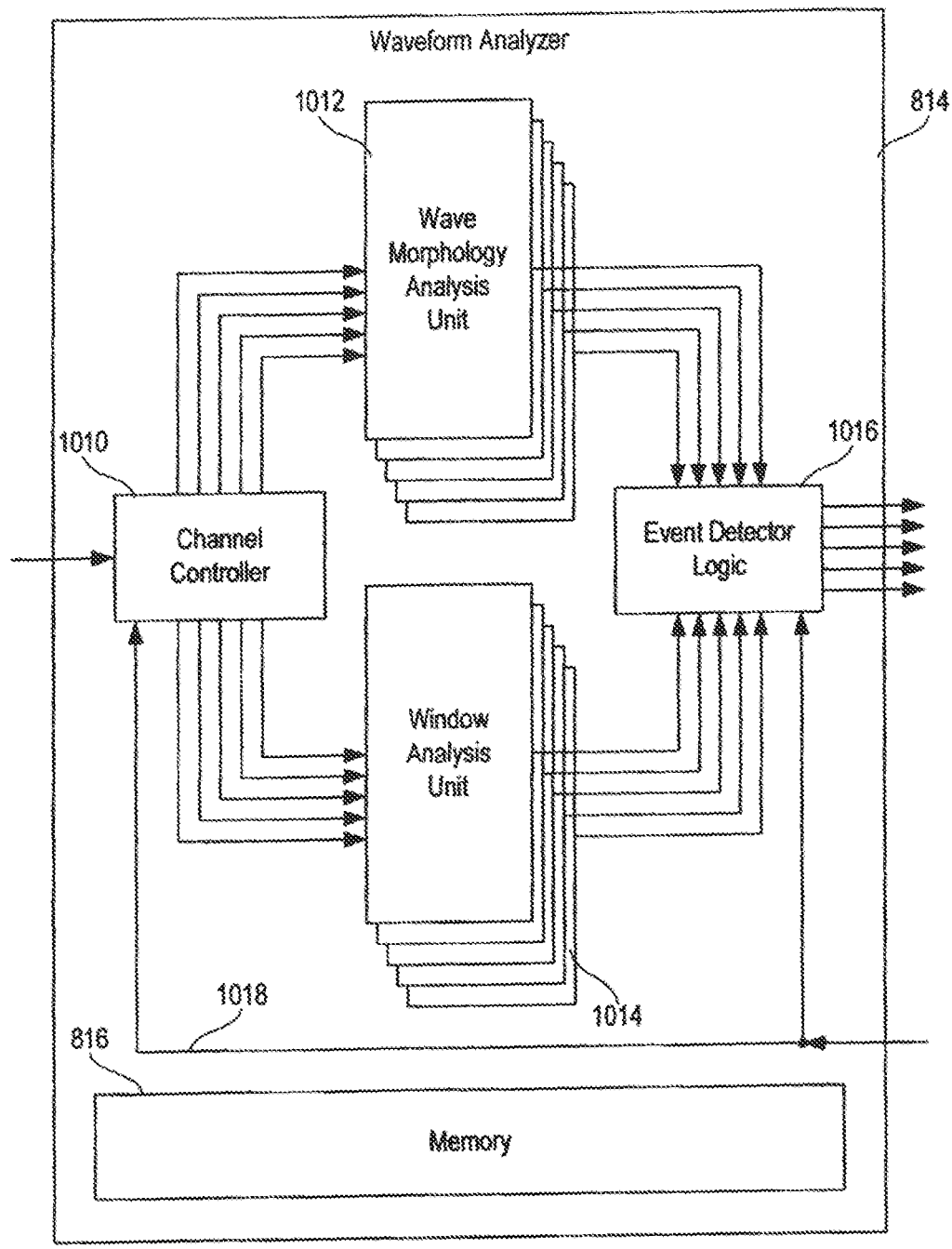
FIG. 10 is a block diagram illustrating the functional components of the waveform analyzer of the detection subsystem of FIG. 8.

In the exemplary waveform analyzer illustrated in FIG. 10, the interleaved digital data stream representing information from all of the active sensing channels is first received by a channel controller 1010. The channel controller applies information from the active sensing channels to a number of wave morphology analysis units 1012 and window analysis units 1014. It is preferred to have as many wave morphology analysis units 1012 and window analysis units 1014 as possible, consistent with the goals of efficiency, size, and low power consumption necessary for an implantable device. In a presently preferred embodiment of the invention, there are sixteen wave morphology analysis units 1012 and eight window analysis units 1014, each of which can receive data from any of the sensing channels of the sensing front end 812 (FIG. 8), and each of which can be operated with different and independent parameters, including differing sample rates, as will be discussed in further detail below. As indicated specifically in parts of this specification, the characteristics measured from signals of different sensing channels can be compared and combined when evaluating the pain signatures, or signatures of other disorders which may be treated using the implantable stimulation device 110.

Each of the wave morphology analysis units 1012 operates to extract certain feature information from an input waveform. The wave morphology analysis units, in the disclosed embodiment of the invention, are configured to detect half waves present in the signal being analyzed. In particular, observed half waves exceeding a specified minimum duration and minimum amplitude are deemed "qualified half waves." If the number of qualified half waves in a specified time period or "window" exceeds a programmed criterion, then the wave morphology analysis unit observing the condition has made a detection. Preferably, hysteresis is accounted for in the determination of half wave start and end points, thereby allowing small signal variations to be largely ignored. For more description of half wave analysis, see U.S. Pat. No. 6,810,285, referenced elsewhere herein.

Similarly, each of the window analysis units 1014 performs certain data reduction and signal analysis within time windows. In an embodiment of the invention, each of the window analysis units calculates "line length" and "area" values and compares these values to programmable thresholds based on longer-term signal trends (though in an embodiment of the invention, static thresholds may also be used). Generalizing to some extent, line length is a measure of signal complexity, while area is a measure of signal power. Details on line length and area-based detection techniques are also set forth in the U.S. Pat. No. 6,810,285.

Output data from the various wave morphology analysis units 1012 and window analysis units 1014 are combined via the event detector logic 1016. The event detector logic 1016 and the channel controller 1010 are controlled by control commands 1018 received from the control interface 818 (FIG. 8).

A "detection channel," as the term is used herein, refers to a data stream including the active sensing front end 812 and the analysis units of the waveform analyzer 814 processing that data stream, in both analog and digital forms. It should be noted that each detection channel can receive data from a single sensing channel; each sensing channel preferably can be applied to the input of any combination of detection channels. The latter selection is accomplished by the channel controller 1010. As with the sensing channels, not all detection channels need to be active; certain detection channels can be deactivated to save power or if additional detection processing is deemed unnecessary in certain applications.

In conjunction with the operation of the wave morphology analysis units 1012 and the window analysis units 1014, a scratchpad memory area 1016 is provided for temporary storage of processed data. The scratchpad memory area 1016 may be physically part of the memory subsystem 426 (FIG. 4) of the device 110 (or a remote sensor or therapy module), or alternatively may be provided for the exclusive use of the waveform analyzer 814 (FIG. 8). Other subsystems and components of a system according to the invention may also be furnished with local scratchpad memory, if such a configuration is advantageous.

The waveform analyzer can also consist of specialized DSP and statistics modules which permit spectral, temporal, and spectro-temporal analysis of signals to permit quantification, classification, and detection of pain signatures as has been described in different areas of this specification. The waveform analyzer can also use control laws in order to generate output stimulation signals based upon the sensed signals. For example, narrowband power of a 0.2-0.4 Hz sensed signal can directly determine the amplitude or duration of the stimulation signal. The control laws can be non-linear and step functions, for example, output stimulation does not occur until the sensed signal is above a specified threshold, and does not increase until the sensed signal is above a second specified threshold, above which a characteristic of the output signal changes according to increases in the power of the sensed signal which is understood to be the pain signature which is being detected.

Figure 11:
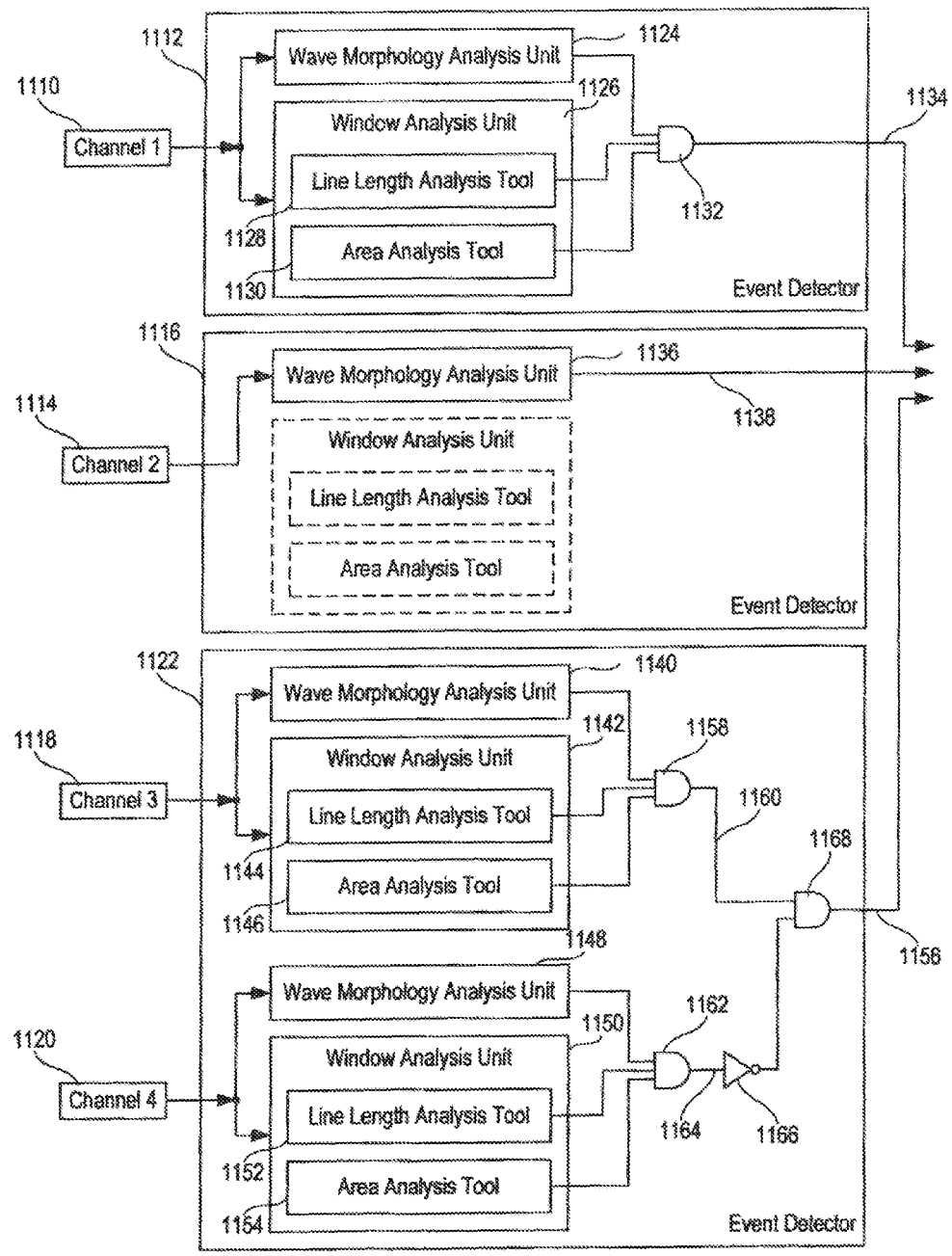
FIG. 11 is a block diagram illustrating the functional arrangement of components of the waveform analysis of the detection subsystem of FIG. 8 in one possible programmed embodiment of the invention.

The operation of the event detector logic 1016 is illustrated in detail in the functional block diagram of FIG. 11, in which four exemplary sensing channels are analyzed by three illustrative event detectors.

A first sensing channel 1110 provides input to a first event detector 1112. While the first event detector 1112 is illustrated as a functional block in the block diagram of FIG. 11, it should be recognized that it is a functional block only for purposes of illustration, and may not have any physical counterpart in a device according to the invention. Similarly, a second sensing channel 1114 provides input to a second event detector 1116, and a third input channel 1118 and a fourth input channel 1120 both provide input to a third event detector 1122.

Considering the processing performed by the event detectors 1112, 1116, and 1122, the first input channel 1110 feeds a signal to both a wave morphology analysis unit 1124 (one of the wave morphology analysis units 1012 of FIG. 10) and a window analysis unit 1126 (one of the window analysis units 1014 of FIG. 10).

The window analysis unit 1126, in turn, includes a line length analysis tool 1128 and an area analysis tool 1130. As described in U.S. Pat. No. 6,810,285, referenced and incorporated by reference above, the line length analysis tool 1128 and the area analysis tool 1130 analyze different aspects of the signal from the first input channel 1110.

Outputs from the wave morphology analysis unit 1124, the line length analysis tool 1128, and the area analysis tool 1130 are combined in a Boolean AND operation 1132 and sent to an output 1134 for further use by a system according to the invention. For example, if a combination of analysis tools in an event detector identifies several simultaneous (or near-simultaneous) types of activity in an input channel, a system according to the invention may be programmed to perform an action in response thereto. Details of the analysis tools and the combination processes used in event detectors according to the invention are set forth in U.S. Pat. No. 6,810,285.

In the second event detector 1116, only a wave morphology analysis unit 1136 is active. Accordingly, no Boolean operation needs to be performed, and the wave morphology analysis unit 1136 directly feeds an event detector output 1138.

The third event detector 1122 operates on two input channels 1118 and 1120, and includes two separate detection channels of analysis units: a first wave morphology analysis unit 1140 and a first window analysis unit 1142, the latter including a first line length analysis tool 1144 and a first area analysis tool 1146; and a second wave morphology analysis unit 1148 and a second window analysis unit 1150, the latter including a second line length analysis tool 1152 and a second area analysis tool 1154. The two detection channels of analysis units are combined to provide a single event detector output 1156.

In the first separate detection channel of the third event detector 1122 including wave morphology analysis unit 1140 and window analysis unit 1142, outputs from the first wave morphology analysis unit 1140, the first line length analysis tool 1144, and the first area analysis tool 1146 are combined via a Boolean AND operation 1158 into a first detection channel output 1160. Similarly, in the second separate detection channel of third event detector 1122 including analysis units 1148 and 1150, outputs from the second wave morphology analysis unit 1148, the second line length analysis tool 1152, and the second area analysis tool 1154 are combined via a Boolean AND operation 1162 into a second detection channel output 1164. In the illustrated embodiment of the invention, the second detection channel output 1164 is invertible with selectable Boolean logic inversion 1166 before it is combined with the first detection channel output 1160. Subsequently, the first detection channel output 1160 and the second detection channel output 1164 are combined with a Boolean AND operation 1168 to provide a signal comprising the output 1156. In an alternative embodiment, a Boolean OR operation is used to combine the first detection channel output 1160 and the second detection channel output 1164.

In one embodiment of the invention, the second separate detection channel of the third event detector 1122 (analysis units 1148 and 1150) represents a "qualifying channel" with respect to the first separate detection channel of the third event detector 1122 (analysis units 1140 and 1142). In general, a qualifying channel allows a detection to be made only when both channels are in concurrence with regard to detection of an event, or when two events are detected approximately at the same time. For example, a qualifying channel can be used to indicate when two separate conditions are occurring in separate parts of the patient's body. To do this, the third input channel 1118 and the fourth input channel 1120 are configured to receive signals from separate amplifier channels coupled to electrodes in separate parts of the patient's brain (e.g., in opposite hemispheres). Accordingly, then, the Boolean AND operation 1168 will indicate a detection only when the first detection output 1160 and the second detection output 1164 both indicate the presence of an event (or, when Boolean logic inversion 1166 is present, when the first detection output 1160 indicates the presence of an event while the second detection output 1164 does not). As will be described in further detail below, the detection outputs 1160 and 1164 can be provided with selectable persistence (i.e., the ability to remain triggered for some time after the event is detected), allowing the Boolean AND combination 1168 to be satisfied even when there is not precise temporal synchronization between detections on the two channels.

It should be appreciated that the concept of a "qualifying channel" allows the flexible configuration of a device 110 according to the invention to achieve a number of advantageous results. In addition to the detection of separate conditions, as described above, a qualifying channel can be configured, for example, to detect noise so a detection output is valid only when noise is not present, to assist in device configuration in determining which of two sets of detection parameters is preferable (by setting up the different parameters in the first detection channel and the second detection channel, then replacing the Boolean AND combination with a Boolean OR combination), or to require a specific temporal sequence of detections (which would be achieved in software by the CPU 428 after a Boolean OR combination of detections). There are numerous other possibilities.

The outputs 1134, 1138, and 1156 of the event detectors are preferably represented by Boolean flags, and as described below, provide information for the operation of a system according to the invention. For example, the outputs 1134, 1138 and 1156 of the three event detectors of a detection subsystem 422 can be routed to a therapy subsystem 424 which uses this information to effect and adjust therapy. The number of outputs which were true can be used to adjust therapy. If output 1134 is true and 1138 and 1156 are false then the therapy delivered may utilize a signal or duration that is one third that which would occur if all the outputs were true, possibly signifying a larger, or at least more global event. Additionally, the outputs 1134, 1138 and 1156 can also determine the location of the stimulation, as would occur if the stimulation occurred only in regions where events were detected, or only at locations where events were not detected, as the case may be, depending upon whether responsive therapy is promoting positive or negative closed-loop feedback, and depending upon whether the stimulation is excitatory or inhibitory to activity in the region to which it is being applied. The therapy subsystem 424 may also change therapy it delivers based upon the duration for which one or more events are detected. As indicated in FIG. 11, the value from the second event detector 1116, can be more than a Boolean result, and may provide a value relating to a characteristic of the event (e.g., size) to the event detection subsystem 422 to the other subsystems of the device 110. Although FIG. 11 shows the outputs from the window analysis unit 1126 and the wave morphology analysis unit 1124 being fed to a Boolean operator 1132, the values of these outputs can also be fed to other circuits, operators, and processes, and can be stored in memory storage. These values are available to other subsystems such as the therapy subsystem 424 which can use the magnitude of these outputs to adjust or create stimulation therapy. One manner of using these outputs is to submit these to modules of the therapy subsystem 424 that enact control laws to produce the stimulation treatment. Accordingly, the stimulation program (duration, site, and type of stimulation), and the stimulation signal itself can be determined, in part, by the characteristics of the pain signature which is detected.

While FIG. 11 illustrates four different sensing channels providing input to four separate detection channels, it should be noted that a maximally flexible embodiment of the present invention would allow each sensing channel to be connected to one or more detection channels. It may be advantageous to program the different detection channels with different settings (e.g., thresholds) to facilitate alternate "views" of the same sensing channel data stream. Accordingly, different detection channels can use different detection, classification, and measurement schemes. Further, the signal processing settings, such as filter settings, may be different for the different channels in order to provide spectral estimates, as has been discussed.

The therapy subsystem 424 of FIG. 4 (and by analogy, the therapy subsystem 722 of FIG. 7) is illustrated in greater detail with reference to FIG. 12.

Figure 12:
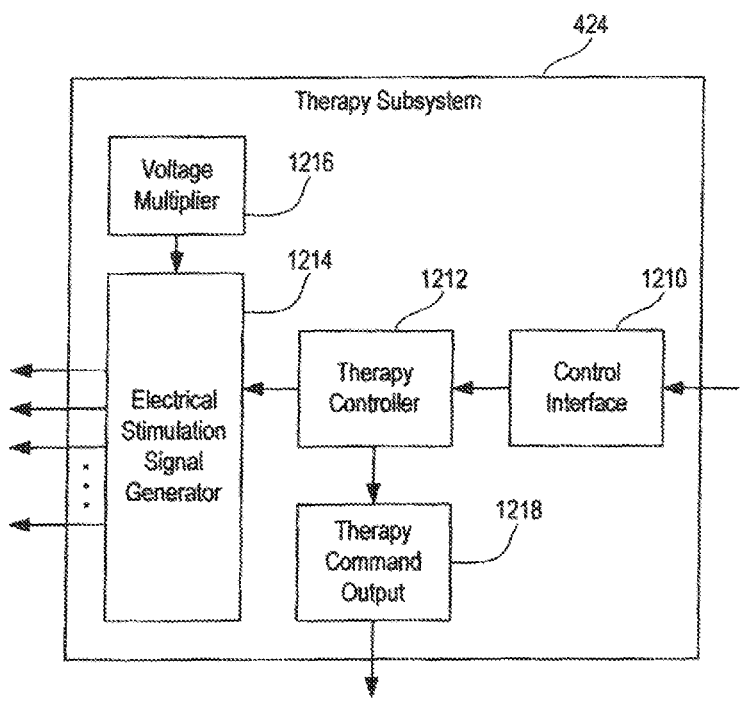
FIG. 12 is a block diagram illustrating the functional components of the therapy subsystem of the implantable neurostimulator shown in FIG. 4.

Referring initially to the input side (right-hand side) of FIG. 12, the therapy subsystem includes a control interface 1210, which receives commands, data, and other information from the CPU 428, the memory subsystem 426, and the detection subsystem 422 (FIG. 4). The control interface 1210 uses the received commands, data, and other information to control a therapy controller 1212. The therapy controller 1212 is adapted to provide stimulation signals appropriate for application as electrical stimulation to neurological tissue to treat a patient's symptoms, and also to generate control signals for drug pumps, thermal stimulators, and other therapy modalities according to the invention. As set forth above, the therapy controller 1212 is typically activated in response to conditions detected by the detection subsystem 422, but may be commanded by an external device, and in an embodiment also provides some substantially continuous or scheduled therapy.

The therapy controller 1212 is coupled to an electrical stimulation signal generator 1214, which in a presently preferred embodiment, allows different stimulation parameters to be selectively applied to the different sensors 412, 414, 416 and 418, either sequentially or substantially simultaneously. The stimulation signal generator 1214 receives commands and data from the therapy controller 1212, and generates electrical stimulation signals having the desired characteristics that are properly time-correlated and associated with the correct electrodes, and receives power from a controllable voltage multiplier 1216 to facilitate the application of a proper voltage and current to the desired neurological tissue. The voltage multiplier 1216 is capable of creating relatively high voltages from a battery power source, which typically has a very low voltage; circuits to accomplish this function are well known in the art of electronics design (and one particular version is set forth in U.S. Pat. No. 6,690,974 to Archer et al. for "Stimulation Signal Generator for an Implantable Device" issued Feb. 10, 2004, which is hereby incorporated by reference as though set forth in full). The stimulation signal generator 1214 has a plurality of outputs, which in the disclosed embodiment are coupled to the sensor interface 420 (FIG. 4). In various embodiments of the invention, the stimulation signal generator 1214 can perform signal isolation, multiplexing, and queuing functions if the sensor interface 420 does not perform such functions.

The therapy controller 1212 is also coupled to a therapy command output 1218. The therapy command output 1218 provides an interface to therapy modalities other than the electrical stimulation provided by the electrical stimulation signal generator 1214. In particular, in an embodiment of the invention, the therapy command output 1218 is coupled to the thermal stimulator 436, the drug dispenser 438, and the optical stimulator 444 (FIG. 4).

It should be recognized that while various functional blocks are illustrated in FIG. 12, not all of them might be present in an operative embodiment of the invention. Furthermore, as with the overall block diagram of FIG. 4 and the remote therapy module 710 of FIG. 7, the functional distinctions illustrated in FIG. 12, which are presented as separate functions for clarity and understandability herein, might not be meaningful distinctions in an implementation of the invention.

Figure 13:
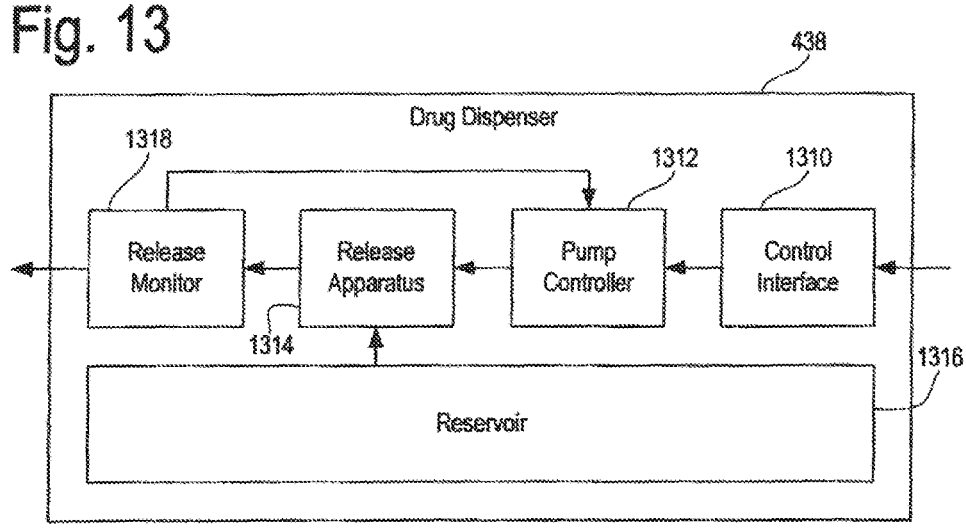
FIG. 13 is a block diagram illustrating the functional components of the drug pump of the implantable neurostimulator shown in FIG. 4.

Elaborating further upon the drug dispenser 438 (FIG. 4) of the device 110 and the drug dispenser 718 of the remote therapy module 710 (FIG. 7), its internal functional breakdown is illustrated somewhat schematically in FIG. 13. The drug dispenser 438 receives input through a control interface 1310—this input is generally received from the therapy subsystem 424 (FIG. 4) and its therapy command output 1218. The drug dispenser 438 is capable of interpreting commands from the therapy subsystem 424 and acting accordingly.

The control interface 1310 drives a pump controller 1312 which, from the commands received and interpreted by the control interface 1310, generates an analog control signal, which in turn controls a release apparatus 1314 comprising, in the disclosed embodiment, a pump and one or more valves. The release apparatus 1314 receives a therapeutic agent (such as a local anesthetic, an analgesic, a corticosteroid, or an opiod) from a reservoir 1316 and delivers the agent through a release monitor 1318 to an output device such as the catheter 442. The release monitor 1318 precisely measures the amount of agent delivered by the drug dispenser 438 and provides information back to the pump controller 1312, thereby allowing regulation of the quantity of therapeutic agent transferred from the reservoir 1316. In an alternative embodiment of the invention, the release monitor may be positioned between the reservoir 1316 and the release apparatus 1314, as long as it is still capable of measuring flow volumes accurately. In yet another embodiment, the release monitor 1318 is not present; the drug dispenser 438 relies upon the precision of the release apparatus 1314 to control the amount of therapeutic agent delivered.

Figure 14:
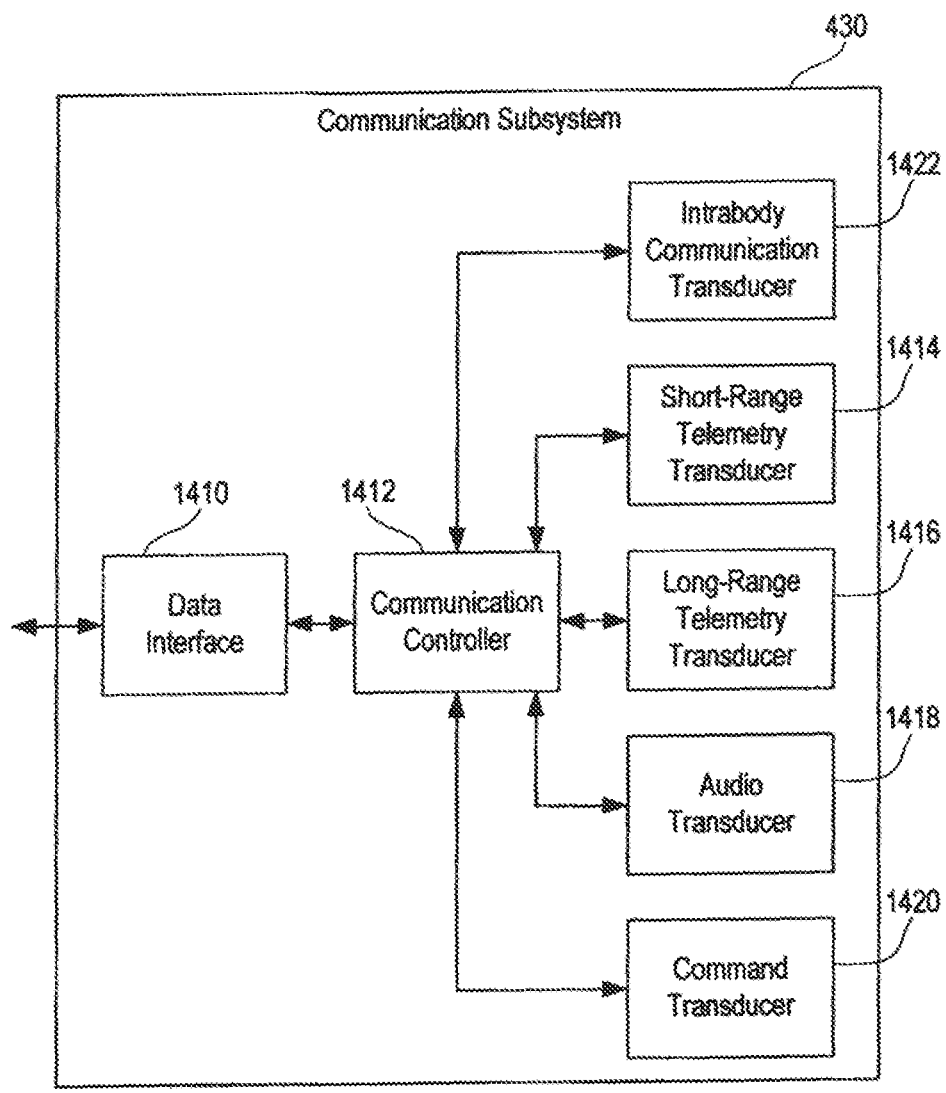
FIG. 14 is a block diagram illustrating the functional components of the communication subsystem shown in FIG. 4.

An embodiment of the communication subsystem 430 (FIG. 4) is illustrated in FIG. 14; the disclosed embodiment enables several different modes of communication intended for different purposes. It will be appreciated that the communication subsystem 430 illustrated in FIG. 14 shares some or all of its components and attributes with the communication subsystem 624 for the remote sensor module 610 and the communication subsystem 728 for the remote therapy module 710.

The communication subsystem 430 includes a data interface 1410 connected and configured to exchange data with the CPU 428 or directly with the memory subsystem 426. The data interface 1410 serves as a selector to enable one or more of the available communication modalities provided for by the invention. The data interface 1410 communicates with a communication controller 1412 interfacing with at least one but in the disclosed embodiment a plurality of transducers 1414, 1416, 1418, 1420 and 1422. The communication controller 1412 enables message queuing, transducer arbitration, protocol translations, and any other necessary steps and functions well known in the art of data communications.

As set forth above, a short-range telemetry transducer 1414 in the disclosed embodiment of the communication subsystem 430 includes a telemetry coil (which may be situated inside or outside of the housing of the implantable neurostimulator device 110) enabling transmission and reception of signals, to or from an external apparatus, via inductive coupling. Short range telemetry is generally effective over distances of only a few centimeters.

An additional transducer provided comprises a long-range telemetry transducer 1416 with an antenna, enabling longer-range (and potentially higher data rate) communications over an RF link. For an implantable device, it is reasonable to expect communication ranges of up to a few meters, possibly more. Relay modules which are either implanted or external to the device may assist in boosting the range of the communication. In an embodiment of the invention, the long-range telemetry transducer operates in the MICS (Medical Implant Communications Service) band at approximately 402-405 MHz. This band is well suited for communication within and around the human body and is available for use in the United States without a license. MICS devices have a very low EIRP (effective isotropic radiated power) limited to 25 microwatts, and hence are considered safe. Integrated circuits enabling MICS communication are commercially available; they may be coupled to a short external pigtail antenna (generally 2-10 cm in length, but other lengths may be used), an external patch antenna, or a patch or trace integrated into a header or housing of the device 110. In an alternative embodiment of the long-range telemetry transducer, a Bluetooth-compatible wireless link may be provided.

An audio transducer 1418 is also provided, though in an embodiment of the invention the audio transducer may be part of the therapy subsystem 424 as described above. As part of the communication subsystem 430, the audio transducer is capable of generating audio signals that can be heard by the patient (for example, as a warning or a programming confirmation), or modulated audio signals (e.g., FSK) for short-range telemetry purposes. A piezoelectric device coupled to a housing 226 (FIG. 2) of the device 110 is well suited for this. The audio transducer in an embodiment of the invention is also capable of receiving and decoding modulated audio signals or audio/tactile input from the patient.

A command transducer 1420 is present, which in the disclosed embodiment of the invention comprises a GMR (giant magnetoresistive effect) sensor to enable receiving simple signals (namely the placement and removal of a magnet) from a patient initiating device according to the invention. Another embodiment of the command transducer 1420 is pressure sensitive. In either case, this input can be used, for example, to enable patient-commanded therapy overrides when pain, numbness, tingling, or other symptom of the disorder is particularly severe and automatic responsive therapy is considered insufficient. This capability is enabled via firmware or software in the device 110. If the therapy subsystem 424 or the communication subsystem 430 includes the audio capability set forth above, it may be advantageous for the communication subsystem 430 to cause an audio signal to be generated upon receipt of an appropriate indication from the patient initiating device (e.g., the magnet used to communicate with the GMR sensor of the communication subsystem 430), thereby confirming to the patient or caregiver that a desired action will be performed.

Finally, an intrabody communication transducer 1422 is available. In an embodiment of the invention, the intrabody communication transducer leverages the capabilities of the long-range telemetry transducer 1416 to enable communication between devices in the human body, such as between a master device 110 and a remote sensor module 610 (FIG. 6) or a remote therapy module 710 (FIG. 7). The MICS band is also appropriate for this purpose; as described above, it is suitable for communication entirely within the body. Alternatively, and somewhat more generally, a near-field electromagnetic radiator and receptor, such as a dipole antenna, can facilitate the modulation of data onto any carrier frequency that is advantageously not absorbed by tissues of the human body, by means well known in the art. The body between dipole antennas serves as the transmission medium between two implanted devices. Sonic communication between audio transducers and receivers is also considered possible; necessary implementation details would be known and understood a practitioner of ordinary skill in sonic intra-device communications in general.

In general, intrabody inter-device communication is preferably limited to intermittent exchanges of short messages to limit power usage. Accordingly, each of the remote sensor modules 610 (FIG. 6) has its own detection subsystem 618 and CPU 622, and each of the remote therapy modules 710 (FIG. 7) is configured with its own therapy subsystem 722 and CPU 726, allowing for semi-autonomous operation when messages are not being exchanged with other devices. However, in an embodiment of the invention, a remote sensor module 610 or a remote therapy module 710 according to the invention may omit much of its internal processing (and memory) in favor of a more heavily used communication link to a master device where processing and analysis is performed. This coordination will be described in further detail below.

A system according to the invention, particularly the neurostimulator device 110, is contemplated to be capable of multiple modalities of therapy. In general, regular or scheduled therapy may be considered advantageous at certain times, and may be scheduled to operate in parallel with responsive therapy modes. Moreover, the neurostimulator device 110 is also gathering data to perform detection and enable therapy refinement in connection with the programmer 312 (FIG. 3) and other external equipment. A basic detection process according to the invention is illustrated in more detail in connection with FIG. 15.

Initially, and continuously, the neurostimulator device 110 measures sensor signals (step 1510) received from the sensors 412, 414, 416 and 418. Various types of sensor data, including electrographic signal waveforms, may be collected by a system according to the invention. Sensors may measure electrographic activity, brain chemistry, temperature, other indicia of physiological conditions and metabolic rate, and patient intent (as indicated by a signal received from the patient initiating device 324 (FIG. 3). Analogously, in a remote sensor module 610, sensor signals are measured from the corresponding sensors 612,614. The sensor signals are analyzed (step 1512) by the detection subsystem 422 and the CPU 428. Generally, custom hardware in the detection subsystem 422 continuously or semi-continuously monitors the sensor signals and provides an interrupt event to the CPU when activity of interest is occurring, allowing the CPU to "wake up" from a low-power state and provide additional processing as needed.

If an event is detected by the CPU (step 1514) according to criteria as described above and illustrated in FIG. 11, an action to be taken in response is identified (step 1516) and then performed (step 1518). The action may include one or more activities, such as continuing to measure (and not applying therapy), storing a record of sensor data for future uploading, applying a therapy locally with the therapy subsystem 424, sending a message to external modules (such as the remote therapy module 710) to intiate therapy, initiating therapy locally, or adjusting stimulation levels locally or remotely to accommodate changed detection levels as described above. The information gathered in measuring (step 1510) and analyzing (step 1512) may also be summarized and transmitted to a remote sensor module 610 to confirm detection of an event of interest.

Figure 15:
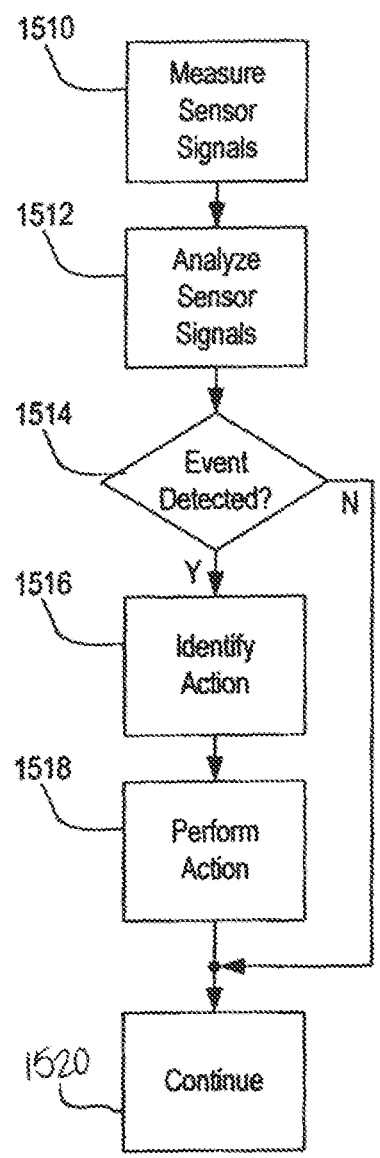
FIG. 15 is a flow chart setting forth an illustrative process performed by hardware and software functional components of the neurostimulator of FIG. 4 in treating pain according to the invention.

As set forth above, the delivery of therapy as an action in FIG. 15 has an effect that extends beyond the immediate duration of the therapy. The duration may vary from patient to patient, however, and therapy according to the invention may be optimized by applying a dose of therapy (such as a burst of electrical stimulation) and waiting for the appropriate detection conditions to occur again, or if therapy is ongoing, adjusting its level to account for changed detection conditions (e.g., a change in level of the observed thalamic oscillations). In an embodiment of the invention, the device receives input from the patient on the duration of relief and suppresses therapy during that interval.

If no event is detected (step 1514), the device continues (step 1520) and carries on with the measurement (step 1510) and analysis (step 1512) of sensor signals.

Although most of the foregoing description pertains most directly to the device 110 illustrated functionally in FIG. 4, it also applies to other devices and modules according to the invention capable of measuring sensor signals and detecting events therein. It should further be noted that the event-driven and parallel processing nature of the device 110 allows for other types of functions by the neurostimulator device 110 to be performed essentially simultaneously with the detection function, such as administrative functions. The nature of these additional functions would be understood by an engineer competent in designing real-time systems.

Figure 16:
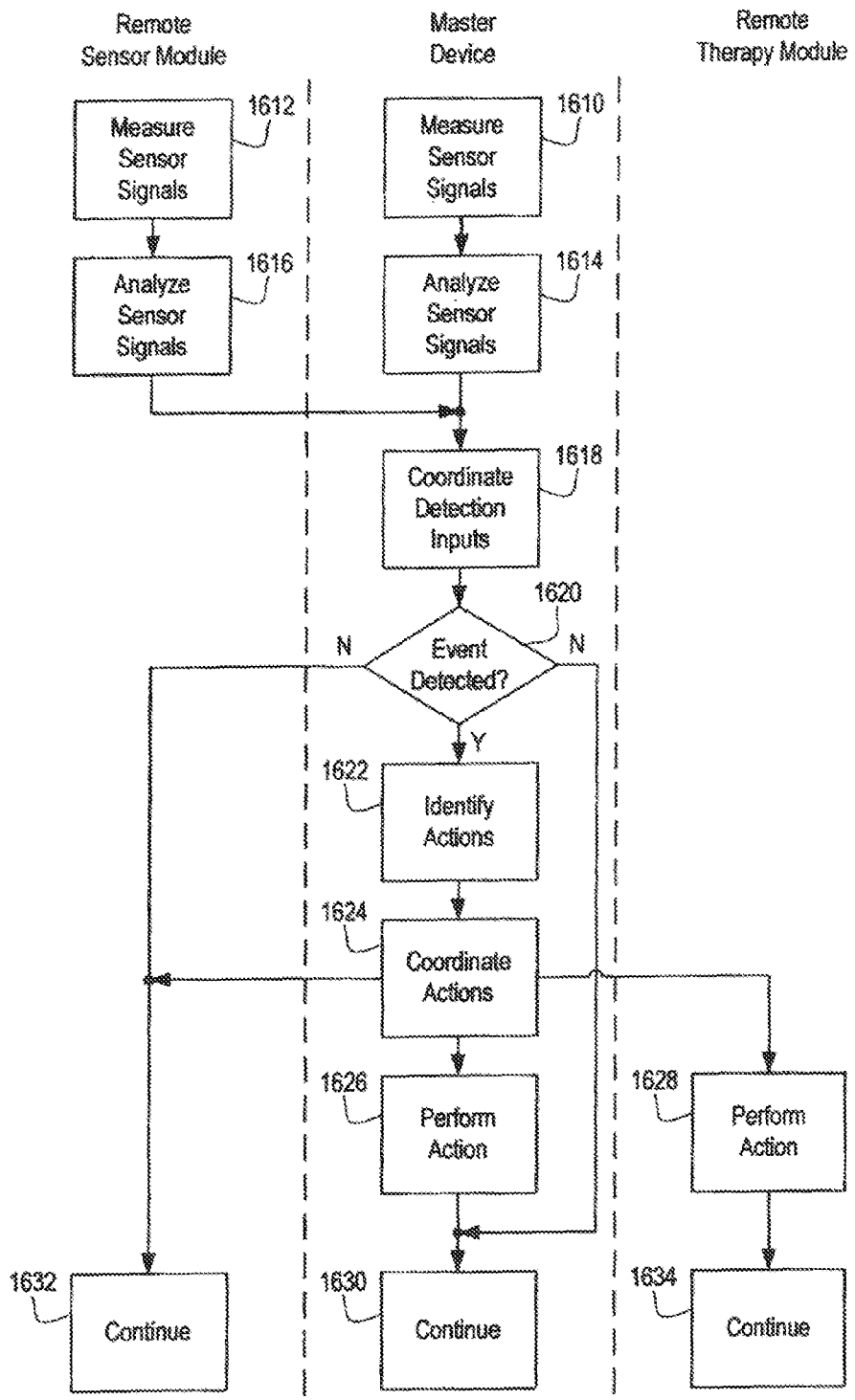
FIG. 16 is a flow chart setting forth an illustrative process performed by hardware and software functional components of the neurostimulator of FIG. 4, in connection with a remote sensing module according to FIG. 6 and a remote therapy module according to FIG. 7 in an embodiment of the invention.

Considering the detection and therapy process in more detail, with the coordination of multiple modules, processes performed by an exemplary embodiment of the invention using a master device such as the neurostimulator device 110, a remote sensor module 610, and a remote therapy module 710, are illustrated in FIG. 16.

As in FIG. 15, sensor signals are monitored by the device 110 (step 1610) and the remote sensor module 610 (step 1612) essentially continuously, and those signals are analyzed by both the device 110 (step 1614) and the remote sensor module 610 (step 1616) as needed. When an event of interest is noted in either the device 110 or the remote sensor module 610, inputs relating to the event are coordinated by the device 110 (step 1618). In an embodiment of the invention, an event detection in a remote sensor module 610 causes the remote sensor module 610 to transmit a message via its communication subsystem 624 to the device 110. Advantageously, the message may contain information about the detected event (such as its magnitude, location, precise timing, or some other parameter of interest) but alternatively the message indicates only that an event occurred.

Coordination of detection inputs as described herein combines and correlates the information received from the remote sensor module 610 with information obtained from the analysis (step 1614) performed locally on the master device 110. The combination and correlation, in an embodiment of the invention, comprises a simple Boolean combination of inputs (event occurs in the master device AND the remote sensor module, or the event occurs in the master device OR the remote sensor module, as configured) with a selectable persistence for both detections as described above. In an alternative embodiment, a detection-related parameter received from the remote sensor module 610 is combined via a mathematical transform, (e.g., multivariate equation), with a parameter observed by the device 110, and that combination is compared to a criterion to determine whether an event of interest has occurred. Further details will be set forth below in conjunction with FIGS. 17-18.

If such an event has been detected (step 1620), the master device 110 identifies the appropriate actions to perform (step 1622) and those actions are coordinated among the relevant portions of the system (step 1624). In the disclosed embodiment, an action is identified (step 1622) and performed (step 1626) by the master device 110 and an action is identified (step 1622) and performed (step 1628) by the remote therapy module 710.

As described above, the step of performing an action (step 1626) may include such as continuing to measure (and not applying therapy), storing a record of sensor data for future uploading, applying a therapy locally with the therapy subsystem 424, sending a message to external modules (such as the remote therapy module 710) to initiate therapy, initiating therapy locally, or adjusting (via feedback) stimulation levels locally or remotely to accommodate changed detection levels.

In coordinating actions to be performed (step 1624), the programming of the device 110 preferably considers clinically relevant criteria (e.g., which may be related to detection of a particular pain signature), including but not limited to the types of therapy that are effective at various locations reachable by the modules in use, time synchronization of multiple therapies (where advantageous), and relief from multiple symptoms and components of chronic pain and other disorders as described generally above.

Whether or not an event has been detected (step 1620), the device 110 continues (step 1630) by measuring sensor signals (step 1610), the remote sensor module 610 continues (step 1632) by also measuring sensor signals (step 1612), and the remote therapy module 710 continues (step 1634) by awaiting further commands from the device 110. It will be recognized that the continuing measurement activities may proceed in any or all of the modules of the invention while therapy and other actions are being performed.

For example, in an embodiment of the invention, as described above in connection with FIG. 5, one or more modules may operate independently or in a coordinated fashion to detect activity and apply therapy in multiple locations. The scenarios set forth in the context of FIG. 5 are illustrative. Where sensing occurs in a single location and therapy in multiple locations in the brain, a master device (for processing and therapy) in conjunction with a remote sensing module may be an effective combination of resources, where the master device coordinates therapy. In this manner, different types of therapy may be used by one or more devices to suppress sensory and affective components of pain. Where sensing occurs in multiple locations and therapy occurs in multiple locations, plural remote sensing modules and remote therapy modules may be coordinated by a single master device, or multiple master devices may be used independently (without intrabody communication) to independently treat multiple symptoms or conditions.

Cognitive effects of pain may be controlled by sensing or providing therapy in the anterior cingulate gyms, the posterior parietal cortex, or the prefrontal cortex, which tend to be activated when pain is experienced. Attention, stress, and arousal may tend to modulate the patient's response to pain.

It will be recognized that it may be advantageous in some circumstances to employ multiple strategies even for a single component of pain. Multiple pain signatures may be observed and tied to different therapies using different devices, stimulation protocols, and stimulation signals. This may occur, in part, using multiple control laws each of which dictates a type of stimulation based upon sensing of a particular pain signature. The therapies may be coordinated or independent.

Figure 17:
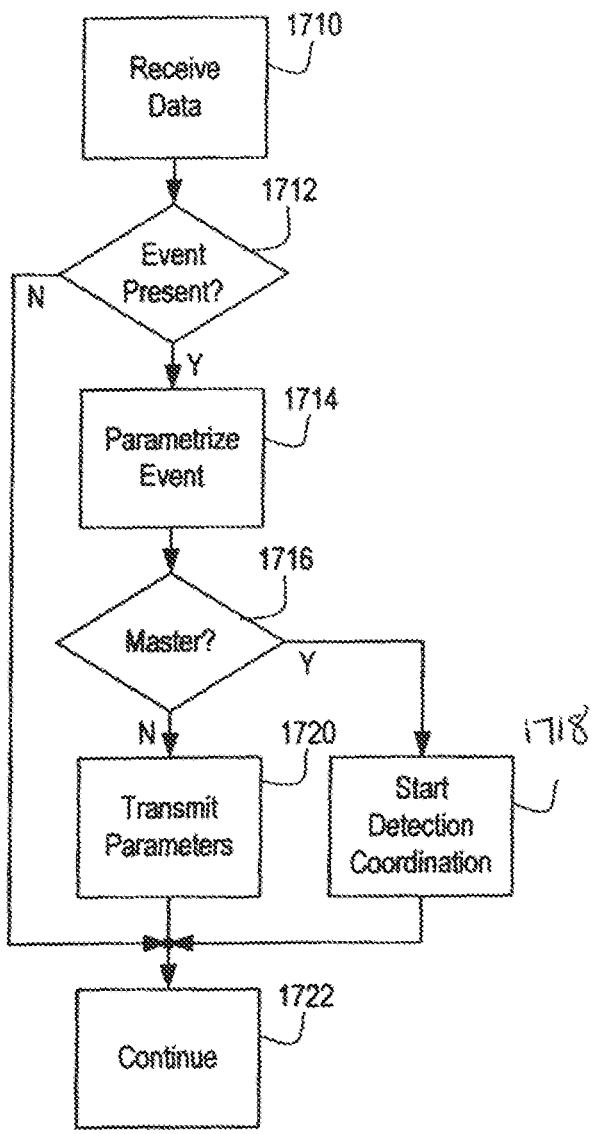
FIG. 17 is a flow chart illustrating an illustrative signal processing flow as performed by a neurostimulator or remote sensing module according to the invention.

A process leading up to coordinating detection inputs (FIG. 16, step 1618) is illustrated in additional detail in FIG. 17. The disclosed process can be performed by any module of a system according to the invention having measurement and detection capabilities, including the neurostimulator device 110 (FIG. 1) and the remote sensor module 610 (FIG. 6).

Initially, as previously discussed, the device 110 or remote sensor module 610 measures and analyzes sensor signals, sending data to the CPU 428 or 622 (step 1710). If the CPU determines that an event has been observed (step 1712), the event is parameterized (step 1714), i.e., reduced to one or more parameters representing useful information about the event. If the device having received the data and observed the event is the master device 110 (step 1716), then detection coordination as described above commences (step 1718). Otherwise, the device is a remote module such as the remote sensor module 610, and the parameters obtained from the event are transmitted to the master device 110 (step 1720). In either case, the device 110 or module 610 continues (step 1722) as set forth above.

Figure 18:
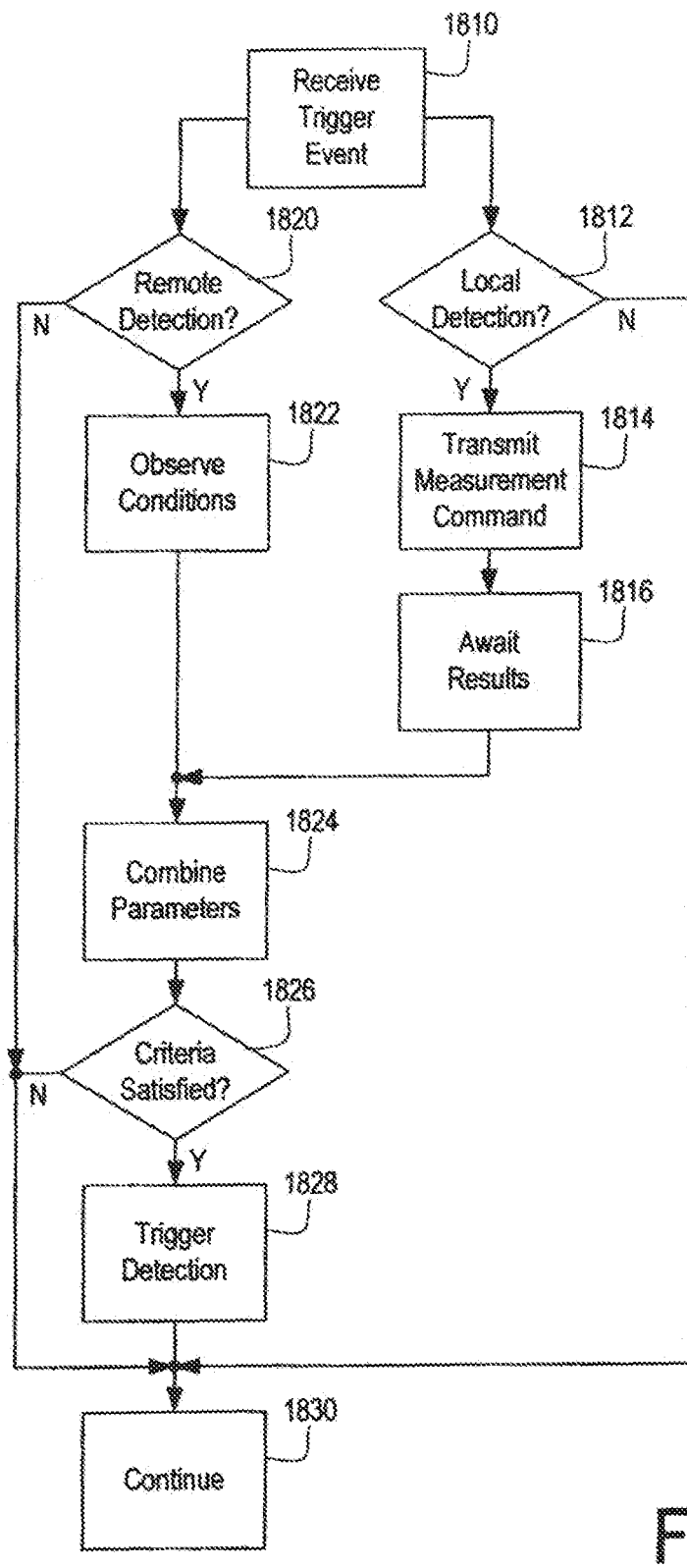
FIG. 18 is a flow chart illustrating a process advantageously used by a system according to the invention to coordinate detection and actions among multiple neurostimulators, remote sensing modules, and remote therapy modules according to the invention.

A process of coordinating multiple detection inputs by a system according to the invention (FIG. 16, step 1618) is illustrated in additional detail in FIG. 18. As described elsewhere herein, devices according to the invention are generally event-driven (and more specifically are interrupt-driven computing devices), thereby facilitating messaging and synchronization among multiple modules.

A device according to the invention having measurement and detection capabilities, including the neurostimulator device 110 (FIG. 1) and the remote sensor module 610 (FIG. 6), initially receives a trigger event (step 1810). If the trigger event is a local event from the detection subsystem 422 or the CPU 428 of the device 110 (step 1812), the device then requests a measurement from one or more remote modules (such as the remote sensor module 610) by transmitting a measurement command (step 1814) and awaiting results (step 1816).

If the trigger event is a remote event (step 1820) received from the communication subsystem 430 (and typically originally transmitted by a remote module such as the remote sensor module 610), the device 110 then observes local conditions (step 1822).

In both cases, parameters obtained from the local measurement and the remote measurement are combined into an overall metric (step 1824). As described above, this combination can be a simple Boolean combination, with or without persistence, or may be a mathematical transform of the two or more inputs. Additionally, the parameters may be submitted to a model, algorithm, multivariate equation, classification or pattern matching subroutine, a neural net or to two or more serial or parallel computations which may include logical operators: any of these may result in one or more metrics, indices, or probabilities. These results can be used to determine or adjust the neurostimulation treatment. The parameters and these results can also be submitted to one or more control laws which can be used to provide neurostimulation at one or more leads.

One or more combinations, indices, or probabilities are compared to a detection criterion (step 1826), and if that criterion is satisfied, a detection is triggered (step 1828) and the system coordinates actions accordingly. These actions can be determined, in part, by the characteristics of the event that was detected (such as peak amplitude, duration, or other indicia of severity, for example) and the results of the operations and transforms used to evaluate these characteristics. Thereafter, in all cases, the device continues (step 1830), waiting for another trigger event to occur.

Figure 19:
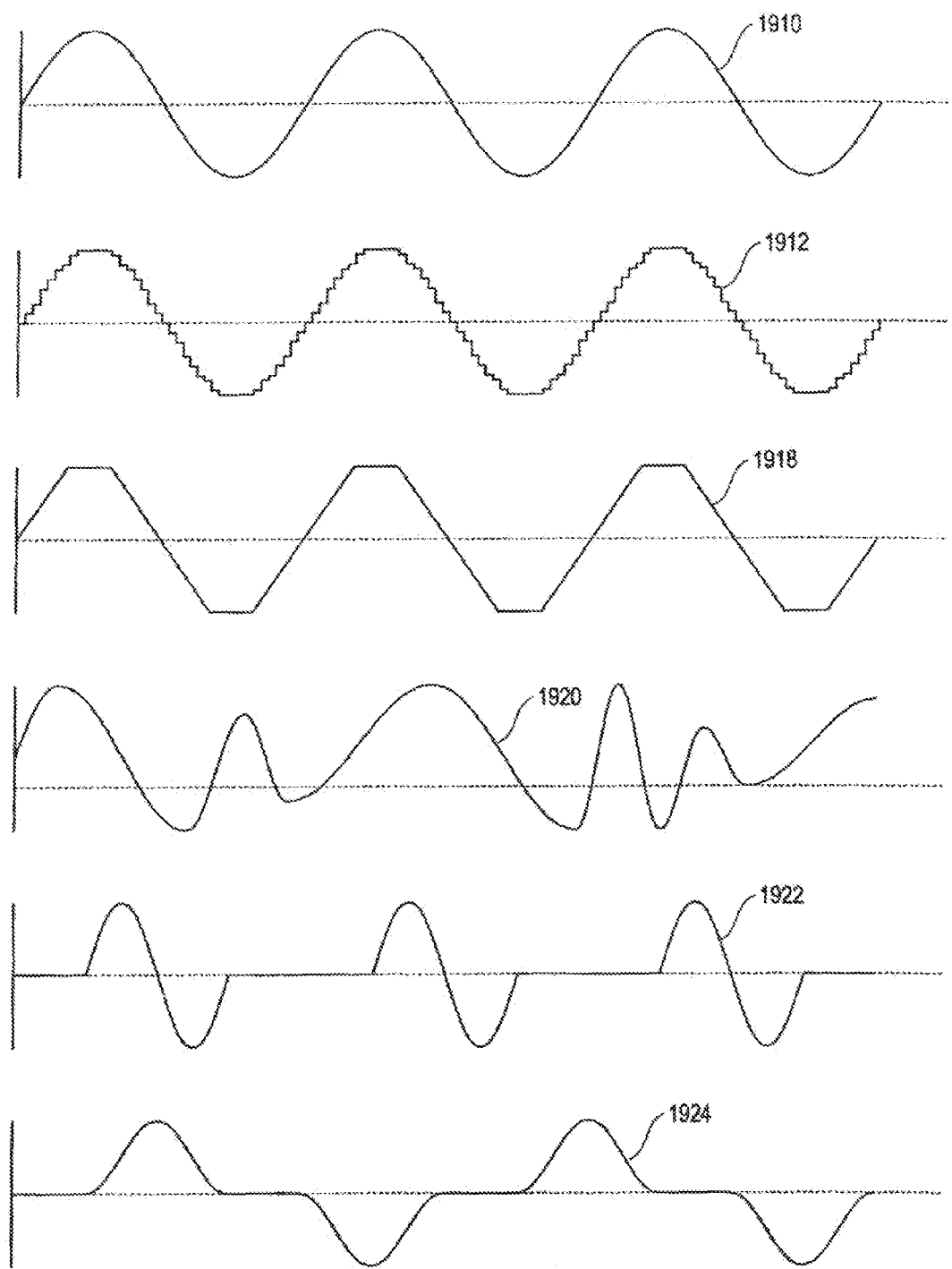
FIG. 19 illustrates an exemplary set of waveforms usable for low-frequency electrical stimulation in an embodiment of the invention.

Referring now to FIG. 19, in addition to traditional biphasic pulse waveforms used for neurostimulation, other wave morphologies may have advantageous applications herein. A sinusoidal stimulation signal 1910 can be produced and used for non-responsive or responsive brain or nerve stimulation according to the invention. In general, sinusoidal and quasi-sinusoidal waveforms may be delivered at low frequencies to have an inhibitory effect, where low frequencies are 0.5 to 10 Hz delivered for 0.05 to 60 minutes at a time. Such waveform may be applied as a result of determining that inhibition is desired on a scheduled basis, or after conditions indicate that responsive stimulation should be applied. Higher frequency sinusoidal or quasi-sinusoidal waveforms may be used for activation. Even higher frequency sinusoidal or pulsatile stimulation may tend to simulate the effects of lesioning (but reversibly), more or less blocking the function of the target structure.

Amplitudes in the range of 0.1 to 10 mA would typically be used for non-pulsatile stimulation (with higher amplitudes possible for short-pulse biphasic pulsatile stimulation), but attention to safe charge densities is important to avoid neural tissue damage. A conservative charge density limit for pulsatile stimulation is about 25 $\mu C/cm^2$ per phase, but for sinusoidal stimulation the limit is expected to be considerably higher. It should be noted that the inhibitory and activating functions of various sinusoidal stimulation parameters may vary when applied to different parts of the brain; the above is merely exemplary.

Sinusoidal and quasi-sinusoidal waveforms presented herein would be constructed digitally by the therapy subsystem 424 (FIG. 4) of the implantable neurostimulator device 110. As a result, the sinusoid 1910 is really generated as a stepwise approximation, via a series of small steps 1912. The time between steps is dependent upon the details of the waveform being generated, but an interval on the order of 40 microseconds has been found to be a useful value. It is anticipated that the stair step waveform 1912 may be filtered to arrive at a waveform more similar to 1910, which would allow for longer periods of time between steps and larger steps. Likewise, for the waveforms 1918, 1920, 1922 and 1924

(described below), it is assumed that they may be created with a series of steps notwithstanding their continuous appearance in the figures.

A truncated ramp waveform 1918 is also possible, where the rate of the ramp, the amplitude reached and the dwell at the extrema are all selectable parameters. The truncated ramp has the advantage of ease of generation while providing the physiological benefits of a sinusoidal or quasi-sinusoidal waveform.

A variable sinusoidal waveform 1920 where the amplitude and frequency are varied while the waveform is applied is also illustrated. The rate and amplitude of the variation may be varied based upon a predefined plan, or may be the result of the implanted neurostimulator sensing signals from the brain during application or between applications of the waveform, and adjusting to achieve a particular change in the sensed signals. The variable waveform 1820 is illustrated herein as having a positive direct current component, but it should be noted that this waveform, as well as any of the others described herein as suitable for use according to the invention, may or may not be provided with a direct current component as clinically desired.

Waveforms 1922 and 1924 depict variations where the stimulating waveform is generated having a largely smooth waveform, but having the additional feature where the interval between waveforms is set by varying a selectable delay, as would be used with the traditional biphasic pulse waveforms described previously. In waveform 1922, the stimulating waveforms are segments of a sine wave separated in time (of course, the same technique could be used for the truncated ramp, or other arbitrary morphologies). Waveform 1924 shows a variation where the derivative in time of the waveform approaches zero as the amplitude approaches zero. The particular waveform 1924 is known as a haversine pulse.

Although the term "haversine pulse" is useful to describe the waveform of 1924, it should be noted that all of the waveforms represented in FIG. 19 are considered herein to be generally "non-pulsatile," in contrast with waveforms made up of traditional discontinuous (e.g. square) pulses. As the term is used herein, "non-pulsatile" can also be applied to other continuous, semi-continuous, discontinuous, or stepwise approximated waveforms that are not exclusively defined by monophasic or biphasic square pulses.

In the disclosed embodiment, the default stimulation behavior provided by a neurostimulator according to the invention is to stimulate with charge-balanced biphasic pulses. This behavior is enforced by stimulation generation hardware that automatically generates a symmetric equal-current and equal-duration but opposite-polarity pulse as part of every stimulation pulse; the precise current control enabled by the present invention makes this approach possible. However, the neurostimulator is preferably programmable to disable the automatic charge balancing pulse, thereby enabling the application of monophasic pulses (of either polarity) and other unbalanced signals.

Alternatively, if desired, charge balancing can be accomplished in software by programming the neurostimulator to specifically generate balancing pulses or signals of opposite phase. Regardless of whether charge balancing is accomplished through hardware or software, it is not necessary for each individual pulse or other waveform component to be counteracted by a signal with identical morphology and opposing polarity; symmetric signals are not always necessary. It is also possible, when charge balancing is desired, to continuously or periodically calculate the accumulated charge in each direction and ensure that the running total is at or near zero over a relatively long term and preferably, that it does not exceed a safety threshold even for a short time.

To minimize the risks associated with waveforms that are either unbalanced or that have a direct current component, it is advantageous to use electrodes having enhanced surface areas. This can be achieved by using a high surface area material like platinum black or titanium nitride as part or all of the electrode. Some experimenters have used iridium oxide advantageously for brain stimulation, and it could also be used here. See Weiland and Anderson, "Chronic Neural Stimulation with Thin-Film, Iridium Oxide Electrodes," *IEEE Transactions on Biomedical Engineering*, 47: 911-918 (2000).

An implantable version of a system according to the invention advantageously has a long-term average current consumption on the order of 10 microamps, allowing the implanted device to operate on power provided by a coin cell or similarly small battery for a period of years without need for replacement. It should be noted, however, that as battery and power supply configurations vary, the long-term average current consumption of a device according to the invention may also vary and still provide satisfactory performance.

It should be observed that while the foregoing detailed description of various embodiments of the present invention is set forth in some detail, the invention is not limited to those details and an implantable neurostimulator device or system made according to the invention can differ from the disclosed embodiments in numerous ways. In particular, it will be appreciated that embodiments of the present invention may be employed in many different applications to responsively treat various pain disorders and both acute and chronic pain conditions as well as adjunct symptoms that arise due to the disorder. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. An implantable system for treating pain in a patient, the system comprising:
  a master module configured to be implanted at or near a first location, the master module including:
    a master communications subsystem,
    a master therapy subsystem, and
    a master detection subsystem configured to identify a first pain signature based at least in part on signals sensed at or near a first detection location, and to initiate application of a therapy in response to confirmation of a pain signature; and
  a remote module configured to be implanted at or near a second location, the remote module including:
    a remote communications systems, and
    at least one of a remote therapy subsystem, and a remote detection subsystem, the remote detection subsystem configured to: obtain information corresponding to one or more of signals sensed at or near a second detection location, and/or to identify a second pain signature based on signals sensed at or near the second detection location.

2. The system of claim 1, wherein the master detection subsystem is configured to initiate application of a therapy through the master therapy subsystem.

3. The system of claim 2, further comprising a therapy output configured to be implanted at or near a first therapy location and coupled to the master therapy subsystem, the therapy output being configured to deliver the therapy.

4. The system of claim 3, wherein the therapy output comprises an electrical stimulation electrode, a magnetic stimulator, a transcranial magnetic stimulator, an optical stimulator, a catheter coupled to a drug dispenser, or a thermal conductor coupled to a thermal stimulator.

5. The system of claim 1, wherein the master detection subsystem is configured to initiate application of a therapy through the remote therapy subsystem, the initiation implemented over a communication link between the master communications subsystem and the remote communications subsystem.

6. The system of claim 5, further comprising a therapy output configured to be implanted at or near a second therapy location and coupled to the remote therapy subsystem, the therapy output being configured to deliver the therapy.

7. The system of claim 1, wherein the remote detection subsystem is configured to transmit a message to the master detection subsystem over a communication link between the master communications subsystem and the remote communications subsystem, the message including information corresponding to one or more of: parameters of signals sensed at or near the second detection location, or an indication of an identified second pain signature.

8. The system of claim 7, wherein the master detection subsystem is configured to confirm a pain signature based on both the signals sensed at or near the first detection location and the parameters of signals sensed at or near the second detection location.

9. The system of claim 7, wherein the master detection subsystem is configured to confirm a pain signature when both of a first pain signature and a second pain signature are identified.

10. The system of claim 7, wherein the master detection subsystem is configured to confirm a pain signature when either one of a first pain signature or a second pain signature is identified.

11. The system of claim 1, wherein the first detection location and the second detection location are remote from each other.

12. The system of claim 1, wherein the first therapy location and the second therapy location are remote from each other.

13. The system of claim 1, wherein each of the first pain signature and the second pain signature comprise at least one of an electrical burst, an electrographic pattern indicative of activation, an electrographic pattern indicative of inhibition, and an oscillating signal.

14. An implantable system for treating pain in a patient, the system comprising:
a master module configured to be implanted at or near a first location, the master module including:
a master communications subsystem,
a master therapy subsystem, and
a master detection subsystem configured to identify a first pain signature based at least in part on signals sensed at or near a first detection location, and to initiate application of a therapy in response to confirmation of a pain signature; and
a remote module configured to be implanted at or near a second location, the remote module including:
a remote communications systems, and
at least one of a remote therapy subsystem, and a remote detection subsystem, the remote detection subsystem configured to: obtain information corresponding to one or more of signals sensed at or near a second detection location, and/or to identify a second pain signature based on signals sensed at or near the second detection location,
wherein each of the master detection subsystem and the remote detection subsystem processes respective sensed signals to identify a respective first pain signature and a second pain signature by being further configured to:
obtain a measure of spectral energy in the respective sensed signals; and
compare the measure to a respective criterion indicative of a pain signature.

15. An implantable system for treating pain in a patient, the system comprising:
a master module configured to be implanted at or near a first location, the master module including:
a master communications subsystem,
a master therapy subsystem, and
a master detection subsystem configured to identify a first pain signature based at least in part on signals sensed at or near a first detection location, and to initiate application of a therapy in response to confirmation of a pain signature; and
a remote module configured to be implanted at or near a second location, the remote module including:
a remote communications systems, and
at least one of a remote therapy subsystem, and a remote detection subsystem, the remote detection subsystem configured to: obtain information corresponding to one or more of signals sensed at or near a second detection location, and/or to identify a second pain signature based on signals sensed at or near the second detection location,
wherein the master detection subsystem is configured to confirm a pain signature when:
both of a first pain signature and a second pain signature are identified, or
either one of a first pain signature or a second pain signature is identified.

* * * * *

UNITED STATES PATENT AND TRADEMARK OFFICE
CERTIFICATE OF CORRECTION

PATENT NO. : 9,114,260 B2
APPLICATION NO. : 14/321287
DATED : August 25, 2015
INVENTOR(S) : Benjamin D Pless and Michael Sasha John Page 1 of 1

It is certified that error appears in the above-identified patent and that said Letters Patent is hereby corrected as shown below:

On the title page item (60),

Related U.S. Application Data reads:

(60)   Continuation of application No. 14/043,599, filed on Oct. 1, 2013, now Pat. No. 8,805,520, which is a continuation of application No. 13/011,917, filed on Jan. 23, 2011, now Pat. No. 8,583,239, which is a division of application No. 11/374,380, filed on Mar. 13, 2006, now Pat. No. 7,894,805.

Related U.S. Application Data should read:

(60)   Continuation of application No. 14/043,599, filed on Oct. 1, 2013, now Pat. No. 8,805,520, which is a continuation of application No. 13/011,917, filed on Jan. 23, 2011, now Pat. No. 8,583,239, which is a division of application No. 11/374,380, filed on Mar. 13, 2006, now Pat. No. 7,894,905.

Signed and Sealed this
First Day of March, 2016

Michelle K. Lee
*Director of the United States Patent and Trademark Office*